US008809268B2

(12) United States Patent
Aroian et al.

(10) Patent No.: US 8,809,268 B2
(45) Date of Patent: Aug. 19, 2014

(54) COMBINATION THERAPY TO COMBAT HELMINTH RESISTANCE

(75) Inventors: Raffi V. Aroian, San Diego, CA (US); Yan Hu, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 413 days.

(21) Appl. No.: 13/126,709

(22) PCT Filed: Oct. 29, 2009

(86) PCT No.: PCT/US2009/005864
§ 371 (c)(1),
(2), (4) Date: Jul. 15, 2011

(87) PCT Pub. No.: WO2010/053517
PCT Pub. Date: May 14, 2010

(65) Prior Publication Data
US 2011/0263489 A1    Oct. 27, 2011

Related U.S. Application Data

(60) Provisional application No. 61/109,413, filed on Oct. 29, 2008.

(51) Int. Cl.
*A61K 38/16* (2006.01)
*A61P 33/10* (2006.01)
*A61P 33/00* (2006.01)

(52) U.S. Cl.
USPC ............................................. 514/4.6

(58) Field of Classification Search
None
See application file for complete search history.

(56) References Cited

U.S. PATENT DOCUMENTS

2005/0203034 A1   9/2005  Ahn et al.
2006/0063841 A1*  3/2006  Meyer et al. .................. 514/602
2010/0024075 A1   1/2010  Aroian et al.

FOREIGN PATENT DOCUMENTS

| EP | 0462721 A2 | 12/1991 |
|---|---|---|
| WO | WO-9906568 A1 | 2/1999 |
| WO | WO-9957128 A1 | 11/1999 |
| WO | WO 2007062064 A2 * | 5/2007 |
| WO | WO-2007062064 A2 | 5/2007 |
| WO | WO-2007062064 A3 | 5/2007 |
| WO | WO-2010053517 A2 | 5/2010 |
| WO | WO-2010053517 A3 | 8/2010 |

OTHER PUBLICATIONS

U.S. Appl. No. 12/085,472, Response filed Feb. 22, 2011 to Restriction Requirement mailed Jan. 19, 2011, 5 pgs.
U.S. Appl. No. 12/085,472, Restriction Requirement mailed Jan. 19, 2011, 6 pgs.
International Application Serial No. PCT/US 2009/005864, Search Report mailed Jul. 1, 2010, 7 pgs.
International Application Serial No. PCT/US 2009/005864, Written Opinion mailed Jul. 1, 2010, 5 pgs.
Aubry, M. L, et al., "Aspects of the pharmacology of a new anthelmintic: pyrantel", Br J Pharmacol., 38(2), (Feb. 1970), 332-44.
Kopp, S. R, et al., "Phenotypic characterization of two *Ancylostoma caninum* isolates with different susceptibilities to the anthelmintic pyrantel", Antimicrob Agents Chemother., 52(11), (Nov. 2008), 3980-6.
Kotze, A. C, et al., "Toxicity of *Bacillus thuringiensis* to parasitic and free-living life-stages of nematode parasites of livestock.", Int J Parasitol., 35(9), (Aug. 2005), 1013-22.
Wei, J. Z, et al., "*Bacillus thuringiensis* Crystal Proteins that target nematodes", Proceedings of the National Academy of Sciences of the United States of America, 100(5), (Mar. 4, 2003), 2760-2765.
Whalon, M. E, et al., "Bt: mode of action and use.", Arch Insect Biochem Physiol., 54(4), (Dec. 2003), 200-11.
U.S. Appl. No. 12/085,472 , Response filed Apr. 23, 2012 to Final Office Action mailed Feb. 23, 2012, 9 pgs.
U.S. Appl. No. 12/085,472 , Response filed Jul. 11, 2011 to Non Final Office Action mailed May 12, 2011, 14 pgs.
U.S. Appl. No. 12/085,472, Advisory Action mailed Apr. 30, 2012, 2 pgs.
U.S. Appl. No. 12/085,472, Final Office Action mailed Feb. 23, 2012, 16 pgs.
U.S. Appl. No. 12/085,472, Non Final Office Action mailed May 12, 2011, 9 pgs.
U.S. Appl. No. 12/085,472, Non Final Office Action mailed Sep. 30, 2011, 13 pgs.
U.S. Appl. No. 12/085,472, Response filed May 22, 2012 to Final Office Action mailed Feb. 23, 2012, 10 pgs.
U.S. Appl. No. 12/085,472, Response filed Dec. 20, 2011 to Non Final Office Action mailed Sep. 30, 2011, 7 pgs.
Crickmore, N., et al., "Revision of the Nomenclature for the *Bacillus thuringiensis* Pesticidal Crystal Proteins", Microbiology and Molecular Biology Reviews, (09/00/98), 807-813.

(Continued)

*Primary Examiner* — Karlheinz R Skowronek
*Assistant Examiner* — Schuyler Milton
(74) *Attorney, Agent, or Firm* — Schwegman, Lundberg & Woessner, P.A.

(57) ABSTRACT

Pharmaceutical compositions having at least one crystal protein and a nicotinic acetylcholine receptor agonist in amounts effective to inhibit a parasitic worm or helminth infection in a vertebrate or mammal are described. Methods for treating a parasitic worm or helminth infection in a subject are also described. The methods include administering to the subject a therapeutically effective amount of the at least one crystal protein and a nicotinic acetylcholine receptor agonist. The crystal proteins can be isolated from *Bacillus thuringiensis* and include Cry5B, Cry21, Cry14A, Cry6A, and Cry13A. The nicotinic acetylcholine receptor agonist can be from the levamisole family, which include levamisole, pyrantel, and tribendimidine.

10 Claims, 28 Drawing Sheets

(56) References Cited

OTHER PUBLICATIONS

Guo, Suxia, et al., "New Strategy for Isolating Novel Nematicidal Crystal Protein Genes from *Bacillus thuringienis* Strain YBT-1518", Applied and Environmental Microbiology, vol. 74, No. 22, (11/00/08), 6997-7001.

Herman, R. A., et al., "Rapid Digestion of Cry34Ab1 and Cry35Ab1 in Simulated Gastric Fluid", J. Agric. Food Chem., 51, (2003), 6823-6827.

Hu, Yan, et al., "Discovery of a highly synergistic anthelmintic combination that shows mutual hypersusceptibility", Hu et al., Pror Natl Acad Sci USA, 107:5955 (2010), 5955-5960.

Hu, Yan, et al., "The New Anthelmintic Tribendimidine is an L-type (Levamisole and Pyrantel) Nicotinic Acetylcholine Receptor Agonist", hu et al. PLoS Negl Trop Dis., 3:e499 (2009), e499.

U.S. Appl. No. 12/085,472, Non Final Office Action mailed Feb. 6, 2014, 17 pgs.

* cited by examiner

|      | LC50 (µg/ml) | Fiduciary Limits |
|------|--------------|------------------|
| N2   | 8.252        | 6.461-10.417     |
| trb-1 | 5.538       | 4.56-6.681       |
| trb-2 | 3.851       | 3.112-4.708      |
| trb-3 | 5.615       | 4.590-6.778      |

|  | LC50 (µg/ml) | Fiduciary limits |
|---|---|---|
| N2 | 19.917 | 17.741-22.544 |
| trb-2 | 7.017 | 6.314-7.767 |
| trb-3 | 23.819 | 18.665-31.097 |

| | LC50 (µg/ml) | Fiduciary limits |
|---|---|---|
| N2 | 11.712 | 9.127-14.646 |
| bre-2(ye31) | 1.160 | 0.83-1.468 |

COMBINATION THERAPY TO COMBAT HELMINTH RESISTANCE

RELATED APPLICATIONS

This patent application is a U.S. National Stage filing under 35 U.S.C. 371 from International Patent Application Serial No. PCT/US2009/005864, filed Oct. 29, 2009 and published on May 14, 2010 as WO 2010/053517 A2, which claims the priority benefit of U.S. Provisional Application Ser. No. 61/109,413 filed Oct. 29, 2008, the contents of which are incorporated herein by reference in their entirety.

CROSS-REFERENCE TO RELATED APPLICATIONS

This application is related to U.S. application Ser. No. 12/085,472, filed May 23, 2008, which is a U.S. National Stage filing under 35 U.S.C. §371 of International Application PCT/US2006/045106, filed Nov. 22, 2006 and published in English as WO 2007/062064 on May 31, 2007, which claims the benefit of the filing date of U.S. Application Ser. No. 60/739,866, filed on Nov. 23, 2005, and of U.S. Application Ser. No. 60/804,250, filed on Jun. 8, 2006; the disclosures of which applications and publication are hereby expressly incorporated by reference herein in their entirety.

STATEMENT OF GOVERNMENT RIGHTS

This invention was made at least in part with a grant from the U.S. Government (grant R01 AI056189 from the National Institutes of Health). The U.S. Government has certain rights in this invention.

BACKGROUND OF THE INVENTION

Soil-transmitted nematodes (STNs), including hookworm, whipworm, and *Ascaris*, are diseases of the world's most poor and are likely the most common human parasite (Stepek et al., 2006; Keiser and Utzinger, 2008; Hoetz et al., 2008). These parasites infect the gastrointestinal (GI) tracts of 1 in 3 people in the world and may cause as much morbidity as malaria. STN infections in children result in growth ad cognitive stunting and severely impact learning, school attendance, and future income potential. The World Health Assembly (WHA) in 2001 has urged the deworming of 75% at-risk school-aged children. Over 44 million hookworm-infected pregnant women are at an increased risk for premature delivery, low birth weight, maternal ill-health, and maternal death. Recent data suggest STN infections worsen the effects of malaria, HIV, and tuberculosis. STNS are one of the great neglected diseases of our time.

The soil microbe *Bacillus thuringiensis* (Bt) is a gram-positive, spore-forming bacterium characterized by parasporal crystalline protein inclusions. These inclusions often appear microscopically as distinctively shaped crystals and therefore, are referred to as crystal (Cry) proteins. Although harmless to vertebrates, many Cry proteins have been found to be highly toxic to a variety of invertebrate species, including free-living nematodes. In particular, soil transmitted nematodes are a legitimate class of therapeutic targets for Bt Cry proteins, especially in light of the fact that Bt is a soil bacterium that potentially interacts with and/or confronts these pathogens in their shared natural environment. Cry5B, like other Cry proteins, is predicted to have a high safety profile in vertebrates because its receptor is only found in invertebrates (Griffitts et al., Science, 307: 922-925, 2005). Cry5B has been shown to be nematicidal against every free-living nematode it was tested against (Wei et al., 2003) and that, when delivered per os (by mouth), cures hamsters of a human hookworm infection (Cappello et al., 2006 and Aroian et al., WO 2007/062064). These proteins, however, have not yet been approved for use in the treatment of STN infections.

Only four drugs (anthelmintics), which fall into two classes, are approved by the WHA for STN therapy: (1) the benzimidazoles (mebendezole (Meb), albendazole) and nicotinic acetylcholine receptor (nAChR) agonists (levamisole (Lev), pyrantel). The problem with having so few anthelmintic classes is the emergence of parasite resistance. In veterinary medicine, every parasitic nematode has been able to develop resistance to every class of anthelmintic, and for some animals, such as infected sheep, there are no treatment options left (Jabar et al., 2006). Although resistance to anthlemintics is suspected in Australia, Zanzibar, Vietnam, and Mali (Flohr et al., 2007; Stepek et al., 2006), STN resistance in human therapy is not widespread today. Experiences from veterinary helminth programs, however, paint a grim picture of the future if we take no action to prevent the emergence of resistance. This realization, as well as the lack of good anti-whipworm drugs, has evoked urgent and repeated cries for the development of new anthelmintics (e.g., Albonico, 2003; Keiser and Utzinger, 2008). It is therefore urgent that we act now while we still have options.

SUMMARY OF THE INVENTION

In one embodiment, the invention includes pharmaceutical compositions that include at least one crystal protein and a nicotinic acetylcholine receptor agonist in amounts effective to inhibit a parasitic worm or helminth infection in a mammal.

In another embodiment, methods of treating a parasitic worm or helminth infection in a subject are also described. The method includes administering to the subject a therapeutically effective amount of at least one crystal protein and a nicotinic acetylcholine receptor agonist.

In yet another embodiment, methods of treating a parasitic worm or helminth infection in a subject where the infection is caused by a parasitic worm or helminth that is resistant to an anthelmintic are also described. The method includes administering to the subject a therapeutically effective amount of at least one crystal protein. The anthelmintic that the parasitic worm or helminth is resistant to can be a nicotinic acetylcholine receptor agonist. The parasitic worm or helminth that is resistant to the nicotinic acetylcholine receptor agonist can be hypersusceptible to the crystal protein such that the therapeutically effective amount of the crystal protein is less than the amount needed to treat a parasitic worm or helminth that is not resistant to the nicotinic acetylcholine receptor agonist.

In another embodiment, methods of treating a parasitic worm or helminth infection in a subject where the infection is caused by a parasitic worm or helminth that is resistant to a crystal protein are also described. The method includes administering to the subject a therapeutically effective amount of a nicotinic acetylcholine receptor agonist. The parasitic worm or helminth that is resistant to the crystal protein can be hypersusceptible to the nicotinic acetylcholine receptor agonist such that the therapeutically effective amount of the nicotinic acetylcholine receptor agonist is less than the amount needed to treat a parasitic worm or helminth that is not resistant to the crystal protein.

In another embodiment, methods of treating a parasitic worm or helminth infection in a subject are described. The method includes the step of administering to the subject synergistically effective amounts of a crystal protein and a nicotinic acetylcholine receptor agonist. The crystal protein and the nicotinic acetylcholine receptor agonist may have a synergistic effect on the parasitic worm or helminth infection greater than the additive nematicidal effect of each of the crystal protein and the nicotinic acetylcholine receptor agonist administered separately or in combination as predicted by a simple additive effect of the two drugs. In such a case, the synergistically effective amount of the crystal protein is less than the amount needed to treat the parasitic worm or helminth infection if the crystal protein was administered without the nicotinic acetylcholine receptor agonist. Similarly, the synergistically effective amount of the nicotinic acetylcholine receptor agonist is less than the amount needed to treat the parasitic worm or helminth infection if the nicotinic acetylcholine receptor agonist was administered without the crystal protein. The synergistic amount of the crystal protein and of the nicotinic acetylcholine receptor agonist may have a synergism factor (CI value) of less than about 0.9, alternatively less than about 0.85, alternatively less than about 0.8, alternatively less than about 0.75, alternatively less than about 0.7, alternatively less than about 0.65, alternatively less than about 0.6, alternatively less than about 0.55, alternatively less than about 0.5, alternatively less than about 0.45, alternatively less than about 0.4, alternatively less than about 0.35, alternatively less than about 0.3, alternatively less than about 0.25, alternatively less than about 0.2, alternatively less than about 0.15, alternatively less than about 0.1. In addition, the use of two drugs that act synergistically and that define a hypersusceptible pairing would act to preserve the efficacy of both over time because the development of resistance to each one would be predicted to be significantly delayed.

In yet another embodiment, methods of treating a parasitic worm or helminth infection in a subject are described that include the step of administering to the subject synergistically effective amounts of Cry5B and a nicotinic acetylcholine receptor agonist from the levamisole family, which includes but is not limited to levamisole, pyrantel, and tribendimidine. These agonists are thought to mechanistically target nematodes in a manner similar to levamisole, The Cry5B and nicotinic acetylcholine receptor agonists from the levamisole family may have a synergistic effect on the parasitic worm or helminth infection greater than the additive nematicidal effect of each of the Cry5B and nicotinic acetylcholine receptor agonist from the levamisole family administered separately or in combination as predicted by a simple additive effect of the two drugs. In such a case, the synergistically effective amount of the Cry5B is less than the amount needed to treat the parasitic worm or helminth infection if the Cry5B was administered without the nicotinic acetylcholine receptor agonist from the levamisole family. Similarly, the synergistically effective amount of the nicotinic acetylcholine receptor agonist from the levamisole family is less than the amount needed to treat the parasitic worm or helminth infection if the nicotinic acetylcholine receptor agonist from the levamisole family was administered without the Cry5B. The synergistic amount of the Cry5B and of the nicotinic acetylcholine receptor agonist from the levamisole family may have a synergism factor (CI value) of less than about 0.9, alternatively less than about 0.85, alternatively less than about 0.8, alternatively less than about 0.75, alternatively less than about 0.7, alternatively less than about 0.65, alternatively less than about 0.6, alternatively less than about 0.55, alternatively less than about 0.5, alternatively less than about 0.45, alternatively less than about 0.4, alternatively less than about 0.35, alternatively less than about 0.3, alternatively less than about 0.25, alternatively less than about 0.2, alternatively less than about 0.15, alternatively less than about 0.1. In addition, the use of two drugs that act synergistically and that define a hypersusceptible pairing would act to preserve the efficacy of both over time because the development of resistance to each one would be predicted to be significantly delayed.

In yet another embodiment, methods of treating a parasitic worm or helminth infection in a subject are described that include the step of administering to the subject synergistically effective amounts of Cry14A and a nicotinic acetylcholine receptor agonist from the levamisole family, which includes but is not limited to levamisole, pyrantel, and tribendimidine. These agonists are thought to mechanistically target nematodes in a manner similar to levamisole, The Cry14A and nicotinic acetylcholine receptor agonists from the levamisole family may have a synergistic effect on the parasitic worm or helminth infection greater than the additive nematicidal effect of each of the Cry14A and nicotinic acetylcholine receptor agonist from the levamisole family, e.g., tribendimidine, administered separately or in combination as predicted by a simple additive effect of the two drugs. In such a case, the synergistically effective amount of the Cry14A is less than the amount needed to treat the parasitic worm or helminth infection if the Cry14A was administered without the nicotinic acetylcholine receptor agonist from the levamisole family. Similarly, the synergistically effective amount of the nicotinic acetylcholine receptor agonist from the levamisole family is less than the amount needed to treat the parasitic worm or helminth infection if the nicotinic acetylcholine receptor agonist from the levamisole family was administered without the Cry14A. The synergistic amount of the Cry14A and of the nicotinic acetylcholine receptor agonist from the levamisole family may have a synergism factor (CI value) of less than about 0.9, alternatively less than about 0.85, alternatively less than about 0.8, alternatively less than about 0.75, alternatively less than about 0.7, alternatively less than about 0.65, alternatively less than about 0.6, alternatively less than about 0.55, alternatively less than about 0.5, alternatively less than about 0.45, alternatively less than about 0.4, alternatively less than about 0.35, alternatively less than about 0.3, alternatively less than about 0.25, alternatively less than about 0.2, alternatively less than about 0.15, alternatively less than about 0.1. In addition, the use of two drugs that act synergistically and that define a hypersusceptible pairing would act to preserve the efficacy of both over time because the development of resistance to each one would be predicted to be significantly delayed.

In yet another embodiment, methods of treating a parasitic worm or helminth infection in a subject are described that include the step of administering to the subject synergistically effective amounts of Cry21A and a nicotinic acetylcholine receptor agonist from the levamisole family, which includes but is not limited to levamisole, pyrantel, and tribendimidine. These agonists are thought to mechanistically target nematodes in a manner similar to levamisole, The Cry21A and nicotinic acetylcholine receptor agonists from the levamisole family may have a synergistic effect on the parasitic worm or helminth infection greater than the additive nematicidal effect of each of the Cry21A and nicotinic acetylcholine receptor agonist from the levamisole family, e.g., tribendimidine, administered separately or in combination as predicted by a simple additive effect of the two drugs. In such a case, the synergistically effective amount of the Cry21A is less than the amount needed to treat the parasitic worm or helminth infection if the Cry21A was administered without the nicotinic acetylcholine receptor agonist from the levamisole family. Similarly, the synergistically effective amount of the nicotinic acetylcholine receptor agonist from the levamisole family is less than the amount needed to treat the parasitic worm or helminth infection if the nicotinic acetylcholine receptor agonist from the levamisole family was administered without the Cry21A. The synergistic amount of the Cry21A and of the nicotinic acetylcholine receptor agonist from the levamisole family may have a synergism factor (CI value) of less than about 0.9, alternatively less than about 0.85, alternatively less than about 0.8, alternatively less than about 0.75, alternatively less than about 0.7, alternatively less than about 0.65, alternatively less than about 0.6, alternatively less than about 0.55, alternatively less than about 0.5, alternatively less than about 0.45, alternatively less than about 0.4, alternatively less than about 0.35, alternatively less than about 0.3, alternatively less than about 0.25, alternatively less than about 0.2, alternatively less than about 0.15, alternatively less than about 0.1. In addition, the use of two drugs that act synergistically and that define a hypersusceptible pairing would act to preserve the efficacy of both over time because the development of resistance to each one would be predicted to be significantly delayed.

In the above-described compositions and methods, the (at least one) crystal protein can be isolated from *Bacillus thuringiensis*. These include, but are not limited to, Cry5B, Cry21A, Cry14A, Cry6A, or Cry13A. The (at least one) crystal protein includes three-domain crystal proteins (such as Cry21A) and non-three-domain crystal proteins (such as Cry6A). The (at least one) crystal protein could also be a pore-forming toxin or a nematicidal crystal protein. The (at least one) crystal protein could also be a crystal protein having at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, or 95% sequence identity with Cry5B in the toxin domain. The (at least one) crystal protein could be present in the pharmaceutical composition in an amount of about 1 mg to about 1500 mg, alternatively about 5 mg to about 1400 mg, alternatively about 5 mg to about 1300 mg, alternatively about 5 mg to about 1200 mg, alternatively about 5 mg to about 1100 mg, alternatively about 5 mg to about 1000 mg, alternatively about 5 mg to about 900 mg, alternatively about 5 mg to about 800 mg, alternatively about 5 mg to about 700 mg, alternatively about 5 mg to about 600 mg, alternatively about 5 mg to about 500 mg, alternatively about 5 mg to about 400 mg, alternatively about 5 mg to about 300 mg, alternatively about 5 mg to about 200 mg, alternatively about 5 mg to about 100 mg. Similarly, the (at least one) crystal protein could be administered to a subject suffering from a parasitic worm or helminth infection in an amount of about 0.01 mg/kg to about 300 mg/kg, alternatively about 0.01 mg/kg to about 200 mg/kg, alternatively about 0.01 mg/kg to about 100 mg/kg, alternatively about 0.01 mg/kg to about 50 mg/kg, alternatively about 0.01 mg/kg to about 25 mg/kg, alternatively about 0.01 mg/kg to about 10 mg/kg, alternatively about 0.01 mg/kg to about 5 mg/kg, alternatively about 0.01 mg/kg to about 1 mg/kg. The Cry protein could also be delivered as part of a transgenic food crop engineered to express the Cry protein, typically at 0.01%-10% of the total protein in the plant. Such a transgenic food crop could be fed to an infected individual.

Cry5B may be present in a pharmaceutical composition in an amount of about 1 mg to about 1500 mg, alternatively about 1 mg to about 1400 mg, alternatively about 1 mg to about 1300 mg, alternatively about 1 mg to about 1200 mg, alternatively about 1 mg to about 1100 mg, alternatively about 1 mg to about 1000 mg, alternatively about 1 mg to about 900 mg, alternatively about 1 mg to about 800 mg, alternatively about 1 mg to about 700 mg, alternatively about 1 mg to about 600 mg, alternatively about 1 mg to about 500 mg, alternatively about 1 mg to about 400 mg, alternatively about 1 mg to about 300 mg, alternatively about 1 mg to about 200 mg, alternatively about 1 mg to about 100 mg. Cry5B could be administered to a subject suffering from a parasitic worm or helminth infection in an amount of about 1 mg/kg to about 100 mg/kg, alternatively about 1 mg/kg to about 50 mg/kg, alternatively about 1 mg/kg to about 20 mg/kg, alternatively about 1 mg/kg to about 10 mg/kg, alternatively about 1 mg/kg to about 5 mg/kg.

Cry14A may be present in a pharmaceutical composition in an amount of about 1 mg to about 500 mg, alternatively about 1 mg to about 400 mg, alternatively about 1 mg to about 300 mg, alternatively about 1 mg to about 200 mg, alternatively about 1 mg to about 100 mg, alternatively about 1 mg to about 50 mg, alternatively about 1 mg to about 20 mg, alternatively about 1 mg to about 15 mg, alternatively about 1 mg to about 10 mg, alternatively about 1 mg to about 5 mg, alternatively about 1 mg to about 4 mg, alternatively about 1 mg to about 3 mg, alternatively about 1 mg to about 2 mg. Cry14A could be administered to a subject suffering from a parasitic worm or helminth infection in an amount of about 5 µg/kg to about 5 mg/kg, alternatively 5 µg/kg to about 4 mg/kg, alternatively 5 µg/kg to about 3 mg/kg, alternatively 5 µg/kg to about 2 mg/kg, alternatively 5 µg/kg to about 1 mg/kg, alternatively 5 µg/kg to about 750 µg/kg, alternatively 5 µg/kg to about 500 µg/kg, alternatively 5 µg/kg to about 250 µg/kg, alternatively 5 µg/kg to about 100 µg/kg, alternatively about 10 µg/kg to about 75 µg/kg, alternatively about 25 µg/kg to about 5 mg/kg, alternatively about 25 µg/kg to about 4 mg/kg, alternatively about 25 µg/kg to about 3 mg/kg, alternatively about 25 µg/kg to about 2 mg/kg, alternatively about 25 µg/kg to about 1 mg/kg, alternatively about 25 µg/kg to about 750 µg/kg, alternatively about 25 µg/kg to about 500 µg/kg, alternatively about 25 µg/kg to about 250 µg/kg, alternatively about 25 µg/kg to about 100 µg/kg, alternatively about 25 µg/kg to about 75 µg/kg, alternatively about 25 µg/kg to about 50 µg/kg.

Cry21A may be present in a pharmaceutical composition in an amount of about 1 mg to about 1500 mg, alternatively about 1 mg to about 1400 mg, alternatively about 1 mg to about 1300 mg, alternatively about 1 mg to about 1200 mg, alternatively about 1 mg to about 1100 mg, alternatively about 1 mg to about 1000 mg, alternatively about 1 mg to about 900 mg, alternatively about 1 mg to about 800 mg, alternatively about 1 mg to about 700 mg, alternatively about 1 mg to about 600 mg, alternatively about 1 mg to about 500 mg, alternatively about 1 mg to about 400 mg, alternatively about 1 mg to about 300 mg, alternatively about 1 mg to about 200 mg, alternatively about 1 mg to about 100 mg. Cry21A could be administered to a subject suffering from a parasitic worm or helminth infection in an amount of about 1 mg/kg to about 100 mg/kg, alternatively about 1 mg/kg to about 50 mg/kg, alternatively about 1 mg/kg to about 20 mg/kg, alternatively about 1 mg/kg to about 10 mg/kg, alternatively about 1 mg/kg to about 5 mg/kg.

Cry6A may be present in a pharmaceutical composition in an amount of about 20 mg to about 3 g, alternatively about 1 mg to about 2.5 g, alternatively about 1 mg to about 2 g, alternatively about 1 mg to about 1.5 g, alternatively about 1 mg to about 1 g, alternatively about 1 mg to about 750 mg, alternatively about 1 mg to about 500 mg, alternatively about 1 mg to about 400 mg, alternatively about 1 mg to about 300 mg, alternatively about 1 mg to about 200 mg, alternatively about 1 mg to about 100 mg, alternatively about 1 mg to about 50 mg, alternatively about 1 mg to about 20 mg, alternatively about 1 mg to about 15 mg, alternatively about 1 mg to about 10 mg, alternatively about 1 mg to about 5 mg, alternatively about 1 mg to about 4 mg, alternatively about 1 mg to about 3 mg, alternatively about 1 mg to about 2 mg, alternatively about 100 μg to about 2 mg, alternatively about 100 μg to about 1 mg alternatively about 100 μg to about 500 μg. Cry6A could be administered to a subject suffering from a parasitic worm or helminth infection in an amount of about 1 mg/kg to about 60 mg/kg, alternatively about 1 mg/kg to about 40 mg/kg, alternatively about 1 mg/kg to about 20 mg/kg, alternatively about 1 mg/kg to about 10 mg/kg, alternatively about 1 mg/kg to about 5 mg/kg, alternatively about 5 μg/kg to about 2 mg/kg, alternatively 5 μg/kg to about 1 mg/kg, alternatively 5 μg/kg to about 500 μg/kg, alternatively 5 μg/kg to about 250 μg/kg, alternatively 5 μg/kg to about 100 μg/kg.

Cry13A may be present in a pharmaceutical composition in an amount of about 1 mg to about 500 mg, alternatively about 1 mg to about 400 mg, alternatively about 1 mg to about 300 mg, alternatively about 1 mg to about 200 mg, alternatively about 1 mg to about 100 mg, alternatively about 1 mg to about 50 mg, alternatively about 1 mg to about 20 mg, alternatively about 1 mg to about 15 mg, alternatively about 1 mg to about 10 mg, alternatively about 1 mg to about 5 mg, alternatively about 1 mg to about 4 mg, alternatively about 1 mg to about 3 mg, alternatively about 1 mg to about 2 mg. Cry13A could be administered to a subject suffering from a parasitic worm or helminth infection in an amount of about 5 μg/kg to about 5 mg/kg, alternatively 5 μg/kg to about 4 mg/kg, alternatively 5 μg/kg to about 3 mg/kg, alternatively 5 μg/kg to about 2 mg/kg, alternatively 5 μg/kg to about 1 mg/kg, alternatively 5 μg/kg to about 750 μg/kg, alternatively 5 μg/kg to about 500 μg/kg, alternatively 5 μg/kg to about 250 μg/kg, alternatively 5 μg/kg to about 100 μg/kg, alternatively about 10 μg/kg to about 75 μg/kg, alternatively about 25 μg/kg to about 5 mg/kg, alternatively about 25 μg/kg to about 4 mg/kg, alternatively about 25 μg/kg to about 3 mg/kg, alternatively about 25 μg/kg to about 2 mg/kg, alternatively about 25 μg/kg to about 1 mg/kg, alternatively about 25 μg/kg to about 750 μg/kg, alternatively about 25 μg/kg to about 500 μg/kg, alternatively about 25 μg/kg to about 250 μg/kg, alternatively about 25 μg/kg to about 100 μg/kg, alternatively about 25 μg/kg to about 75 μg/kg, alternatively about 25 μg/kg to about 50 μg/kg.

In the above-described compositions and methods, the nicotinic acetylcholine receptor agonist could be from the levamisole family of nicotinic acetylcholine receptor agonists. These nAChR agonists are thought primarily to target the L-type receptor subclass. Members of this family include, but are not limited to, levamisole, pyrantel, and tribendimidine.

Levamisole may be present in a pharmaceutical composition in an amount of about 100 μg to about 500 mg, alternatively about 1 mg to about 500 mg, alternatively about 1 mg to about 400 mg, alternatively about 1 mg to about 300 mg, alternatively about 1 mg to about 200 mg, alternatively about 1 mg to about 100 mg, alternatively about 1 mg to about 50 mg, alternatively about 1 mg to about 25 mg. Levamisole could be administered to a subject suffering from a parasitic worm or helminth infection in an amount of about 0.1 mg/kg to about 50 mg/kg, alternatively about 0.1 mg/kg to about 20 mg/kg, alternatively about 0.1 mg/kg to about 10 mg/kg, alternatively about 0.1 mg/kg to about 5 mg/kg, alternatively about 0.1 mg/kg to about 2.5 mg/kg.

Pyrantel may be present in a pharmaceutical composition in an amount of about 1 mg to about 1200 mg, alternatively about 1 mg to about 1100 mg, alternatively about 1 mg to about 1000 mg, alternatively about 1 mg to about 900 mg, alternatively about 1 mg to about 800 mg, alternatively about 1 mg to about 700 mg, alternatively about 1 mg to about 600 mg, alternatively about 1 mg to about 500 mg, alternatively about 1 mg to about 400 mg, alternatively about 1 mg to about 300 mg, alternatively about 1 mg to about 200 mg, alternatively about 1 mg to about 100 mg. Pyrantel could be administered to a subject suffering from a parasitic worm or helminth infection in an amount of about 1 mg/kg to about 50 mg/kg, alternatively about 1 mg/kg to about 20 mg/kg, alternatively about 1 mg/kg to about 15 mg/kg, alternatively about 1 mg/kg to about 10 mg/kg, alternatively about 1 mg/kg to about 5 mg/kg, alternatively about 1 mg/kg to about 2.5 mg/kg, alternatively about 5 mg/kg to about 20 mg/kg, alternatively about 5 mg/kg to about 15 mg/kg, alternatively about 5 mg/kg to about 10 mg/kg.

Tribendimidine could be present in a pharmaceutical composition in an amount of about 1 mg to about 1200 mg, alternatively about 1 mg to about 1100 mg, alternatively about 1 mg to about 1000 mg, alternatively about 1 mg to about 900 mg, alternatively about 1 mg to about 800 mg, alternatively about 1 mg to about 700 mg, alternatively about 1 mg to about 600 mg, alternatively about 1 mg to about 500 mg, alternatively about 25 mg to about 500 mg, alternatively about 1 mg to about 400 mg, alternatively about 1 mg to about 300 mg, alternatively about 1 mg to about 200 mg, alternatively about 1 mg to about 100 mg, alternatively about 100 mg to about 800 mg, alternatively about 100 mg to about 700 mg, alternatively about 100 mg to about 600 mg, alternatively about 100 mg to about 500 mg, alternatively about 100 mg to about 400 mg. Tribendimidine could be administered to a subject suffering from a parasitic worm or helminth infection in an amount of about 1 mg/kg to about 50 mg/kg, alternatively about 1 mg/kg to about 400 mg/kg, alternatively about 1 mg/kg to about 200 mg/kg, alternatively about 1 mg/kg to about 100 mg/kg, alternatively about 1 mg/kg to about 50 mg/kg, alternatively about 1 mg/kg to about 25 mg/kg, alternatively about 1 mg/kg to about 20 mg/kg, alternatively about 1 mg/kg to about 10 mg/kg, alternatively about 1 mg/kg to about 5 mg/kg, alternatively about 1 mg/kg to about 2.5 mg/kg, alternatively about 5 mg/kg to about 20 mg/kg, alternatively about 5 mg/kg to about 15 mg/kg, alternatively about 5 mg/kg to about 10 mg/kg, alternatively about 0.25 mg/kg to about 10 mg/kg, alternatively about 0.25 mg/kg to about 7.5 mg/kg, alternatively about 0.25 mg/kg to about 5 mg/kg, alternatively about 0.25 mg/kg to about 2.5 mg/kg, alternatively about 0.25 mg/kg to about 1 mg/kg.

In the above-described methods, the parasitic worm or helminth infection can be caused by, but is not limited to, Roundworm, Whipworm, Hookworm, *Ascaris*, Pinworm, *Strongyloides*, Schistosome, and Trematodes. The parasitic worm or helminth infections can be treated in humans and other vertebrates or mammals such as felines, rodents, canines, bovines, equines, swines, caprines, ovines, and primates. In methods in which a crystal protein and a nicotinic acetylcholine receptor agonist are both administered, the crystal protein and the nicotinic acetylcholine receptor agonist can be administered in a single formulation or in separate formulations. Similarly, the crystal protein and the nicotinic acetylcholine receptor agonist could be administered at the same time or sequentially. The use of two drugs that act synergistically and that define a hypersusceptible pairing could act to preserve the efficacy of both over time because the development of resistance to each drug would be predicted to be significantly delayed.

DETAILED DESCRIPTION

Figure 1A:
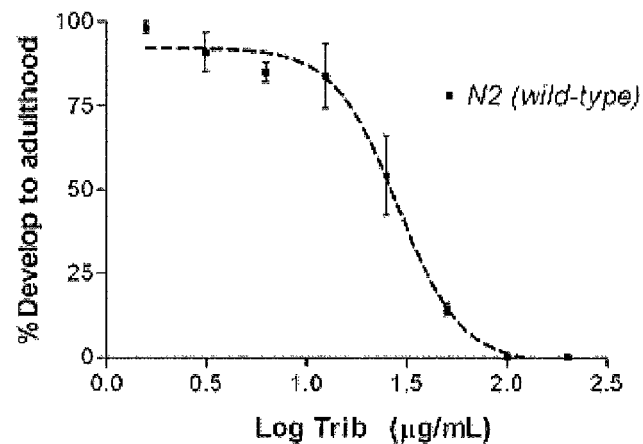
FIG. 1A is a graph of a *C. elegans* larval development assay on tribendimidine (log Trib (μg/ml) vs. % develop to adulthood).

Crystal (Cry) proteins produced by the soil bacterium Bacillus thuringiensis (Bt) are harmless to vertebrates but highly toxic to a variety of invertebrate species. For instance, B. thuringiensis Cry proteins in the Cry5 and Cry6 subclades intoxicate free-living nematodes.

Cry21A and Cry14A are also nematicidal and part of the same clade of proteins as Cry5B and so may be useful in the compositions and methods of the invention. Based on resistance profiles in C. elegans, resistance to Cry21A and Cry5B is via a different pathway in that mutant animals that are highly resistant (>500 fold) to Cry5B relative to wild type are only slightly (2 fold) resistant to Cry21A. Moreover, Cry14A and Cry21A are toxic to the same nematodes that Cry5B intoxicates including the rodent nematode Nippostrongylus. Therefore, a combination of crystal proteins may be employed in a therapeutic treatment, e.g., Cry5B and Cry21A together or Cry14A and Cry21A together, so as to avoid resistance.

The use of Bt crystal proteins is advantageous in that those proteins are safe and non-toxic to vertebrates and unlike currently used anti-nematode compounds, nematode pests are not resistance to Bt crystal proteins. Moreover, crystal proteins may provide an alternative therapy for animal parasitic nematode infections in those cases where resistance to currently used compounds has occurred. Alternatively, co-therapy of crystal protein and currently used compounds, e.g., albendazole, mebendazole, levamisole, ivermectin, pyrantel, or tribendimidine, may provide an advantage as such therapy would be predicted to be resistance-free for a long time. Structures of some of these anthelmintics are reproduced below in TABLE 1.

TABLE 1

Levamisole
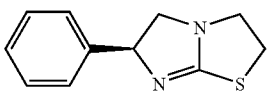

Pyrantel
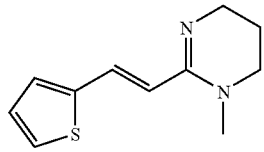

Tribendimidine
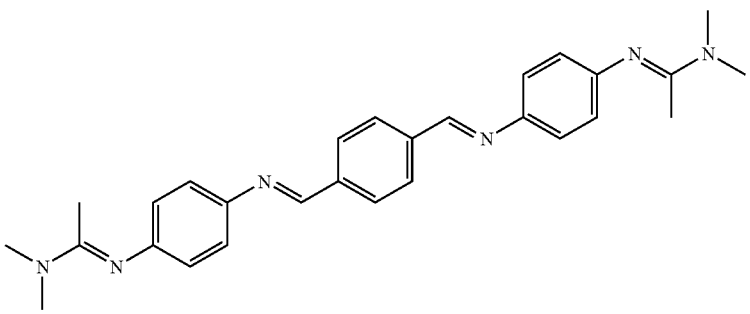

Bt Proteins

*Bacillus thuringiensis* (Bt) crystal (Cry) proteins are the most widely used biologically-produced insecticides in the world (Whalen et al., 2003). Bt is a soil bacterium that produces large crystalline inclusions upon sporulation. These crystals contain one or several Cry proteins that are highly toxic to invertebrates (Naimor et al., 2001; Wei et al., 2003). For decades, Cry proteins have been applied in large quantities to agricultural fields and the environment in order to kill both insects (caterpillars and beetles) that eat plants and insect vectors (mosquitoes and black flies) that transmit viruses and helminthes (Federici, 2005). More recently, transgenic crops expressing Bt Cry proteins have been found to provide strong protection against caterpillars (Federici, 2005). In the year 2005, over 26 million hectares (mha) of Bt crops were planted, including 8.5 mha of Bt cotton, accounting for about 24% of all the cotton grown in the world (James, 2005). The tremendous success of this natural resource is due to multiple factors, including high efficacy, absence of toxicity of Cry proteins towards mammals and other vertebrates, and the ability to produce Cry proteins cheaply and in massive quantities. Bt Cry proteins confer substantial benefit to the environment and farm worker safety by reducing applications of toxic chemical insecticides that adversely affect farm workers, other non-target animals, and the environment (Qaim et al, Hossain et al, Carrier et al).

Three Cry proteins, Cry5B, Cry14A, and Cry21A, that are toxic to both free-living nematodes (roundworms) and the free-living stage of one parasitic nematode, have been identified and characterized (Wei et al., 2003). Vertebrate-safe Cry proteins could be used to treat both human and veterinary nematode infections. In particular, soil transmitted nematodes (STNS) are a legitimate class of therapeutic targets for Bt Cry proteins, since Bt is a soil bacterium that potentially interacts with and/or confronts these pathogens in their shared natural environment. Globally, STN infections represent a major cause of morbidity in developing countries, with an estimated burden of human disease comparable to that of malaria or tuberculosis (Savoili et al., 2004; Chan, 1997; Crompton et al., 2003; deSilva et al., 2003; Molyneux et al., 2005). In addition to human disease, animal nematode infections are of major veterinary significance, resulting in millions of dollars of lost revenue effecting industries that provide products and food from livestock, including cattle and sheep (Coles, 2005; Coles et al., 2005a; Chandrawathani et al., 2003; Mertz et al., 2005; Von Sampson et al., 2005; Wolstenholme et al., 2004; McKellar et al., 2004). In light of well-founded concerns about the emergence of antihelminthic resistance, there exists a pressing need to develop new, safe, and inexpensive agents for the treatment of human and veterinary nematode infections of global significance (Wolsten et al., 2004; Geerts et al., 2001; Albonico, 2003; Albonico et al., 2004; Reynoldson et al., 1997; DeClercq et al., 1997).

Exemplary Parasites

The present invention relates to the control of parasitic worms, e.g., nematodes and platyhelminths, using crystal proteins from *Bacillus* and their derivatives. Parasitic worms within the scope of the invention include but are not limited to those in Class Adenophorea, e.g., Order Mononchida, Family Plectidae, and Order Stichosomida, Family Mermithidae and Tetradonematidae; Class Secernentea, e.g., Order Rhabditida, Family Carabonematidae, Cephalobidae, Chambersiellidae, Heterorhabditidae, Oxyuridae, Panagrolaimidae, Rhabditidae, Steinernematidae, Syrphonematidae, Syrphonematidae, or Thelastomatidae; Order Spirurida, Family Filariidae, Onchocercidae, Physalopteridae, Syngamidae, Spiruridae, Subuluridae, or Thelaziidae; Order Diplogasterida, Family Diplogasteridae; and Order Tylenchida, Family Allantonematidae, Aphelenchidae, Aphelenchoididae, Entaphelenchidae, Fergusobiidae, Phaenopsitylenchidae, Sphaerulariidae, Anguinidae, Dolichodoridae, Belonolaimidae, Pratylenchidae, Hoplolamidae, Heteroderidae, Criconematidae, Tylenchulidae or Tylenehidae. In one embodiment, the parasite is from Class Secernentea, Order Ascaridida, Family Ascarididae; Class Adenophorea, Order Trichurida, Family Trichuridae; Class Secernentea, Order Strongylida, Family Ancylostomatidae (ancylostomidae) or Trichostrongylidae; or Class Secernentea, Order Spirurida, Family Dracunculidae, Filariidae, or Onchocercidae.

In one embodiment, the parasite is a helminth. Helminths within the scope of the invention include but are not limited to those from Phylum Annelida, Class Polychaetae, Class Myzostomida, Class Clitellata, Subclass Hirudinea, Order Gnathobdellidae, Order Rhynchobdellidae; Phylum Platyhelminthes (Flatworms), Class Turbellaria, Class Monogenea, Order Monopisthocotylea, Order Polyopisthocotylea, Class Trematoda, Subclass Aspidogasrea, Subclass Digenea; Super Order Anepitheliocystida, Order Strigeatida, Family Schistosomatidae, Subfamily Schistosomatinae, Genus *Schistosoma*, Order Echinostomatida, Family Fasciolidae, Family Paramphistomatidae, Family Echinostomatidae; Super Order Epitheliocystida, Order Plagiorchiida, Family Dicrocoeliidae, Family Troglotrematidae, Order Opisthorchiida, Family Heterophyidae, Family Opisthorchiidae, Class Cestoda, Subclass Cestodaria, Subclass Eucestoda, Order Pseudophyllidea, Family Diphyllobothriidae, Order Cyclophyllidea, Family Taeniidae, Family Hymenolepididae, Family Dilepididae, Family Mesocestoididae, Order Tetraphyllidea, Order Proteocephalata, or Order Spatheobothridea. For example, Cry proteins with the scope of the invention may be employed to prevent, inhibit or treat Roundworm, Whipworm, Hookworm, Schistosome, or Trematodes.

Pharmaceutical Compositions

As used herein "pharmaceutically acceptable carrier" is intended to include any and all solvents, dispersion media, coatings, antibacterial and antifungal agents, isotonic and absorption delaying agents, anti-inflammatory, stabilizers, and the like, compatible with pharmaceutical administration. The use of such media and agents for pharmaceutically active substances is well known in the art. The indication to be treated, along with the physical, chemical, and biological properties of the drug, dictate the type of formulation and the route of administration to be used, as well as whether local or systemic delivery would be preferred. Except insofar as any conventional media or agent is incompatible with the active compound, use thereof in the compositions is contemplated. Supplementary active compounds can also be incorporated into the compositions. Carrier molecules may be genes, polypeptides, antibodies, liposomes or indeed any other agent provided that the carrier does not itself induce toxicity effects or cause the production of antibodies that are harmful to the individual receiving the pharmaceutical composition. Further examples of known carriers include polysaccharides, polylactic acids, polyglycolic acids and inactive virus particles. Carriers may also include pharmaceutically acceptable salts such as mineral acid salts (for example, hydrochlorides, hydrobromides, phosphates, sulphates) or the salts of organic acids (for example, acetates, propionates, malonates, benzoates). Pharmaceutically acceptable carriers may additionally contain liquids such as water, saline, glycerol, ethanol or auxiliary substances such as wetting or emulsifying agents, pH buffering substances and the like. Carriers may enable the pharmaceutical compositions to be formulated into tablets, pills, dragees, capsules, liquids, gels, syrups, slurries, suspensions to aid intake by the patient. Various formulations and drug delivery systems are available in the art, and a thorough discussion of pharmaceutically acceptable carriers are available in the art (see, e.g., USIP. Remington; The Science and Practice of Pharmacology (Lippincott Williams & Wilkins, 21st ed. 2005); and Ansel & Stoklosa, Pharmaceutical Calculations (Lippincott Williams & Wilkins, 11th ed., 2001)

A pharmaceutical composition used in the methods of the invention is formulated to be compatible with its intended route of administration. Examples of routes of administration include parenteral, e.g., intravenous or intra-arterial, intradermal, subcutaneous, oral or nasal (e.g., inhalation), transdermal (topical), transmucosal, nasal, pulmonary, ocular, gastrointestinal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Alternate routes of administration include intraperitoneal, intra-articular, intracardiac, intracisternal, intradermal, intralesional, intraocular, intrapleural, intrathecal, intrauterine, intraventricular, and the like.

Pharmaceutical dosage forms of a Cry compound of the invention may be provided in an instant release, controlled release, sustained release, target drug-delivery system, or in a transgenic food plant expressing the Cry protein. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks, or presented in the form of implants and pumps requiring incision. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, emulsions and the like. The compounds may also be formulated in rectal compositions, such as suppositories or retention enemas.

Preferably, pharmaceutical compositions suitable for injectable use include sterile aqueous solutions (where water soluble) or dispersions and sterile powders for the extemporaneous preparation of sterile injectable solutions or dispersion. Depending on the injection site, the vehicle may contain water, synthetic or vegetable oil, and/or organic co-solvents. In certain instances, such as with lyophilized product or a concentrate, the parenteral formulation would be reconstituted or diluted prior to administration. Depot formulations, providing controlled or sustained release of an invention compound, may include injectable suspensions of nano/micro particles or nano/micro or non-micronized crystals. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, poly(ol) (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; dissolution retardant; anti-adherants; cationic exchange resin; wetting agents; antioxidants; preservatives; a disintegrating agent such as alginic acid, Primogel, or corn starch; a lubricant such as magnesium stearate or Sterotes; a glidant such as colloidal silicon dioxide; a preservative; a colorant; a sweetening agent such as sugars such as dextrose, sucrose or saccharin; or a flavoring agent such as peppermint, methyl salicylate, or orange flavoring, each of these being synthetic and/or natural. Oral compositions can also include a Cry protein expressed in a food plant that is then fed to the intended recipient.

For administration by inhalation, the compounds are delivered in the form of an aerosol spray from pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams, emulsion, a solution, a suspension, or a foam, as generally known in the art. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustments; use of complexing agents and other techniques, such as iontophoresis, may be used to regulate skin penetration of the active ingredient.

The active agents can also be prepared in the form of suppositories (e.g., with conventional suppository bases such as cocoa butter and other glycerides) or retention enemas for rectal delivery.

In one embodiment, the agents are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Preparation and Assays

Developmental Assay.

The nematode *Caenorhabditis* has been extensively used in the study of anthelmintics (anti-nematode drugs). The reason is that, unlike animal parasitic nematodes, no vertebrate host is needed to grow *C. elegans*. It can be readily and rapidly grown in standard laboratory conditions and is amenable to powerful genetic, molecular, genomic, cell biological, and biochemical studies. The power of this model organism to elucidate fundamental principles of biology is attested to by the fact that the Nobel Prizes in Medicine in 2002 and 2006 and the Nobel Prize in Chemistry in 2008 all included scientists who work in the *C. elegans* field. Because *C. elegans* is a nematode that is amenable to molecular genetics whereas animal parasitic nematodes are not, *C. elegans* has proven invaluable in finding the mechanism of action of anthelmintics (Geary and Thompson, 2001). *C. elegans* is considered an excellent model for anthelmintic mode of action and resistance and has been central in defining the mode of action of most anthelmintics (Holden-Dye and Walker, 2007; Hasmi et al., 2001; Brown et al., 2006). The relevance and importance of *C. elegans* in studying anthelmintics was most recently confirmed in the discovery of a new anthelmintic for use in veterinary animals (Kaminsky et al., 2008). *C. elegans* molecular genetics absolutely predicted the mechanism of resistance in an intestinal parasitic nematode.

The *Caenorhabditis elegans* life cycle has 6 stages: embryonic, first larval (L1), second larval (L2), third larval (L3), fourth larval (L4), and adult. Between each of the larval stages and between the L4 and adult stages, the worms molt (shed) their outer cuticle ("skin"). In a developmental assay, a large population of L1 wild-type (N2) nematodes were isolated. This was done by bleaching (see protocol below). After hatching off in M9 (from end of bleaching protocol), the L1 larvae were spun down in a clinical centrifuge at 1800 rpm for 50 sec and re-suspended in special S Medium (called SS Medium; see recipe below). Aliquots (5 μl) of the nematodes were counted and the volume of the liquid was adjusted to bring the concentration of the L1 larvae to 4 nematodes per 5 μl. The assay was set up in a 48-well microtiter plate. Each of the wells contained: 5 μl L1 nematodes (~20 total), 20 μl of OP50 bacteria as a food source (see below for preparation), 20 μl of drug, and SS Medium to bring the total up to 200 μl. Each well contained a specific dose of drug and that dose was repeated for a total of three times per microtiter plate. The microtiter plate was then wrapped in damp paper towels, placed inside a covered plastic box, and incubated in a 20° C. incubator for 60 h. The microtiter plate was then removed, and the nematodes were transferred from a given well with a glass Pasteur pipette into the well of a spot glass. The number of nematodes that have reached adulthood (as ascertained by the presence of embryos inside the hermaphrodite body) and the number of nematodes that have not reached adulthood were tallied for each well (in the absence of drug, virtually all L1 larvae will make it to adulthood in 60 h at 20 deg C.). The data from triplicate wells were combined into a single data point. The experiment was repeated for a total of three times on three different days (total of 9 wells per data point).

LC50 Assay.

LC50 assays determine the inhibitory concentration at which 50% of the nematodes are dead under certain conditions as calculated using the PROBIT algorithm. LC50 assays start with wild-type (N2) L4 nematodes. To get L4 nematodes, synchronous L1-staged nematodes (as per developmental assay) were plated onto OP50-seeded ENG plates (see below) and put at 20° for 44 h. The now L4-staged larvae were then washed off with water, spun down at 1800 rpm for 40 seconds, re-suspended with SS Media, spun again, and re-suspended in special SS Media to a concentration of 4 nematodes/μl. The assay was set up in a 48-well microtiter plate. Each well contained: 5 μl L4 nematodes (~20 total), 40 μl of OP50 bacteria as a food source (see below for preparation), 20 μl of tribendimidine (prepared as below), 5 μl of FUdR (8 mM stock; see below), and SS Medium for a total of 200 μl. Each well was set up in triplicate. The plates were wrapped in moist paper towels, placed in a covered plastic box, and incubated at 25° C. for 6 days. The plates were then removed from the incubator and the nematodes transferred with a glass pipette into the well of a spot glass. Each nematode was then scored for dead or alive as follows. Using a thin platinum wire, each nematode was touched to see if it moved within 10 seconds of being touched. If it moved, it was scored as alive. If not, the touch was repeated a second time. If it moved after the second touch, it was scored as alive. If it did not move upon the second touch, it was scored as dead. The number of alive and dead nematodes was tallied for each well. The data from triplicate wells were combined into a single data point. The experiment was repeated for a total of three times on three different days (so a total of 9 wells per data point).

Bleaching and Worm Preparation.

The worms were bleached and prepared for the assays according to the following steps. A 60-mm NG plate full of gravid adults was washed twice with 2 ml $H_2O$. The washes were combined in a 15-ml conical tube and centrifuged at 500 g for 45 s. The supernatant was aspirated, 5 ml of $H_2O$ was added, and the preparation was spun as before. The supernatant was again aspirated. Bleaching solution (2 ml) was added and then mixed by hand. Worm lysis was monitored on a dissecting scope, with occasional mixing. When worms were fully lysed and eggs were released (typically takes 4-8 min), $H_2O$ (5 ml) was added. The lysate was centrifuged and aspirated as before. The preparation was washed with additional $H_2O$ (5 ml) and then washed with M9 (5 ml). Because the eggs do not pellet as well in M9 as in water, the eggs were spun for 75 s at 750 g. The supernatant was carefully removed with a pipette and the M9 wash (5 ml) was repeated. Following this last wash, the eggs were re-suspended in M9 (1 ml). The tube was then placed on a rotary platform and the eggs were allowed to hatch overnight at room temperature.

Preparation of *Escherichia coli* OP50 Food Source.

A colony of OP50 was grown overnight in Luria-Bertani (LB) broth. The OD600 (optical density of liquid medium at 600 nm) was measured relative to LB standard. The LB media was centrifuged at 3500 rpm for 5 minutes, washed once with SS Media, pelleted, and re-suspend in SS Media with correct volume calculated to give an OD600 of 3.0.

Preparing Tribendimidine Stock.

A tribendimidine stock solution was prepared at 4 mg/ml at 1% DMSO in SS Media (final concentration in the well will be 0.1% DMSO). 1% DMSO in SS Media was used as a dilutant to set up serial dilutions. For example, tube 1 contained 160 μl of 4 mg/ml Trib in 1% DMSO. Tube 2 contained 80 μl of the solution in Tube 1, diluted with 80 μl 1% DMSO (1:1 dilution; tube 2). Tube 3 contained 80 μl of the solution from Tube 2, diluted with 80 microliters 1% DMSO, etc. . . .

Bleaching Solution.

The bleaching solution was prepared fresh by combining 3.5 ml dd$H_2O$ (double distilled water), 0.5 ml 5 M KOH, and 1 ml 4-6% sodium hypochlorite (standard household bleach).

M9 Buffer:

The M9 buffer contains: 2.2 mM $KH_2PO_4$, 4.2 mM $Na_2HPO_4$, 85.6 mM NaCl, 1 mM $MgSO_4$. The M9 buffer is prepared in ddH2O without the $MgSO_4$ and autoclaved. Sterile $MgSO_4$ is then added and the buffer is stored at room temperature.

S Basal:

S-basal contains: 0.1 M NaCl, 0.05 M KHPO4 (pH 6.0). S-basal was prepared in dd$H_2O$, autoclaved, and stored at room temperature.

Trace Metals Solution:

The trace metals solution contains: 5 mM EDTA, 2.5 mMFeSO4, 1 mM MnCl2, 1 mM ZnSO4, 0.1 mM CuSO4. The trace metals solution was prepared in ddH$_2$O, autoclaved, and stored in the dark at room temperature.

S Medium:

S medium was prepared by combining 10 ml S basal with 0.1 ml 1 M potassium citrate (pH 6.0), 0.1 ml trace metals, 0.03 ml 1 M CaCl$_2$, 0.03 ml 1 M MgSO$_4$, and 0.01 ml 5 mg cholesterol/ml (in ethanol). All components were sterile.

Special S Medium:

Special S medium was prepared by combining 10 ml S basal with 0.1 ml 1 M potassium citrate (pH 6.0), 0.1 ml trace metals, 0.03 ml 1 M MgSO4, and 0.01 ml 5 mg cholesterol/ml (in ethanol). All components were sterile. The pH of the medium was raised to 7.3 with KOH. Note, Special S medium differs from standard S Medium in its pH and in the absence of CaCl$_2$.

Nematode Growth (NG) Plates:

NG plates were prepared by mixing 972 ml of ddH$_2$O, 3 g NaCl, 2.5 g bacto peptone (Becton, Dickinson, and Company, Sparks, Md.), and 20 g bacto agar (Becton, Dickinson, and Company). The mixture was autoclaved inside a flask containing a stir bar. After autoclaving, the solution was mixed on a stir plate. When the solution cooled to about 50° C., the following sterile reagents were added: 1 ml of 5 mg cholesterol/ml (prepared in ethanol), 1 ml 1 M CaCl2, 1 ml 1 M MgSO4, and 25 ml 1 M potassium phosphate (pH 6.0). An aliquot (12 ml) of solution was placed in each 60 mm Petri dish. After plates dried for 1-2 d, a few drops of a saturated *E. coli* OP50 culture as a food source were added.

Enriched Nematode Growth (ENG) Plates:

ENG plates were prepared as described above for NG plates except that ENG plates also contain 5 g bacto peptone (instead of 2.5 g) and additionally 1 g bacto yeast extract (Becton, Dickinson, and Company) for 972 ml of water. Aliquots of 40 ml are added per 100-mm dish. Approximately 250 µl of an *E. coli* OP50 culture were spread per plate and incubated overnight at 37° C.

5-Fluoro-2'-Deoxy-Uridine (FUdR):

FUdR is a drug that prevents the production of progeny in adult nematodes that might otherwise kill the mother by hatching internally or interfere with the scoring. A 100 mM stock in ddH$_2$O was prepared and diluted in SS medium to a final concentration of 8 mM prior to use in the assay.

Brood Size Assay:

L4 staged worms were used. One worm was picked up with an eyelash pick and placed in SS Media in a 48-well plate. Each well also contained: 40 µl OD$_{600}$ 3.0 OP50 and 10 µl Cry5B in 20 mM Hepes buffer as pH 8.0 as before. The total volume was 200 µl. Each drug concentration was repeated in triplicate. The plates were incubated for 64 h at 25° C. The progeny were then transferred out of the well with a pipette onto an empty NG agar plate for counting. The experiment was repeated a total of three times.

*C. Elegans* is Susceptible to Tribendimidine

FIG. 1A depicts the response of *C. elegans* nematodes to the drug tribendimidine as measured by the effect of the drug on their development. The larval development assay was performed as described above. Each well contained a specific dose of tribendimidine and that dose was repeated for a total of three times per microtiter plate. The results of this assay showed that as the concentration of tribendimidine increased, fewer L1 nematodes were able to complete development to the adult stage in 60 h at 20° C. The IC50 (inhibitory concentration at which 50% of the larvae are unable to complete development at these conditions) is 18.38 µg/ml of tribendimidine. The fiduciary limits represent the 95% confidence limits on this value.

Figure 1B:
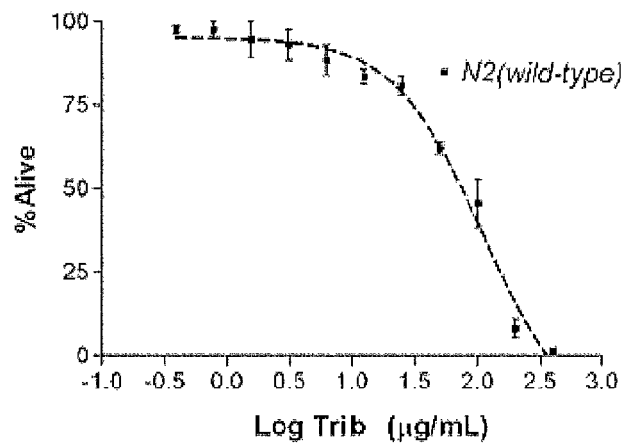
FIG. 1B is a graph of the response of C. elegans to tribendimidine as measured by the effect on viability (log Trib (μg/ml) vs. % alive).
Figure 2:
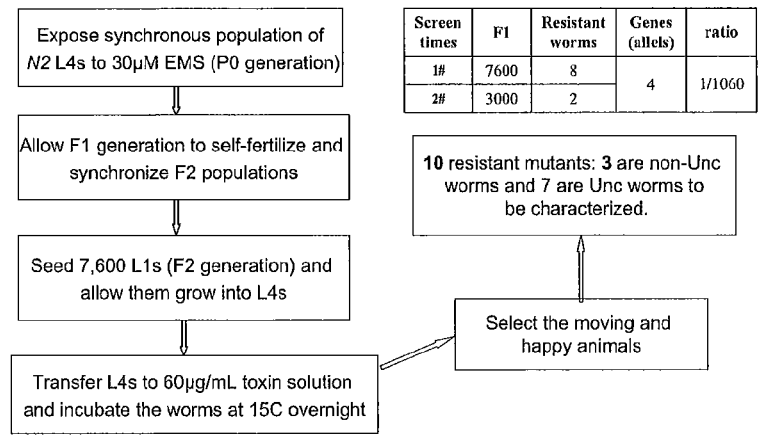
FIG. 2 is a flow chart showing two genetic screens to identify tribendimidine-resistant mutants.

FIG. 1B shows the response of *C. elegans* nematodes to the drug tribendimidine as measured by the effect of the drug on their viability. The results of this assay show that, as the concentration of tribendimidine increases, fewer nematodes were able to survive for 6 days at 25° C. The LC50 is 54.38 µg/ml of tribendimidine. The fiduciary limits represent the 95% confidence limits on this value.

*C. elegans* Mutants Isolated for their Resistance to Tribendimidine

To find *C. elegans* nematodes resistant to tribendimidine, a large synchronous population of L4-staged-wild-type nematodes (obtained as described above) were incubated in 30 µM EMS (ethyl methane sulfonate) in M9 for 4 hours at room temperature. The mutagenzied nematodes were then rinsed and pelleted in M9 four times and plated onto ENG plates at 20° C. overnight. The next day, F1 (first generation) embryos were isolated from the mutagenized nematodes by bleaching. The F1 embryos were hatched off overnight in M9 and then plated onto ENG plates and grown until gravid adult stage at 20° C. for 3 days. F2 (second generation) embryos were then isolated from the F1 adults by bleaching and were allowed to hatch off overnight in M9. The L1 larvae of the F2 were then plated onto ENG plates and grown until the L4 stage (2 days, 20° C.). The L4 staged larvae (F2) were then put into 48-well plates with 60 µg/ml tribendimidine and incubated at 15° C. overnight. Any nematodes that appeared motile were then transferred out of the wells and grown on NG plates. The progeny from these candidate-resistant nematodes were then placed onto NG plates containing 100 µg/ml tribendimidine. From two similar genetic screens, a total of 10 confirmed tribendimidine-resistant mutants ("trb") were identified. The total number of equivalent mutagenized F1 nematodes screened to isolate these 10 mutants was 10,600. These 10 mutants were then crossed with one another. To do this, either homozygous males or heterozygous males from the strains were obtained and these were crossed into the other strains to perform complementation testing (example of how such testing is carried out can be found in Marroquin et al., 2000, *Genetics* v. 155: 1693-1699, which is hereby incorporated by reference in its entirety). The results of these crosses showed that the 10 mutants defined four different complementation groups (or genes) identified in TABLE 2.

TABLE 2

| Mutant | No. of Alleles |
| --- | --- |
| trb-1 | 5 |
| trb-2 | 1 |
| trb-3 | 1 |
| trb-4 | 3 |

Figure 3:
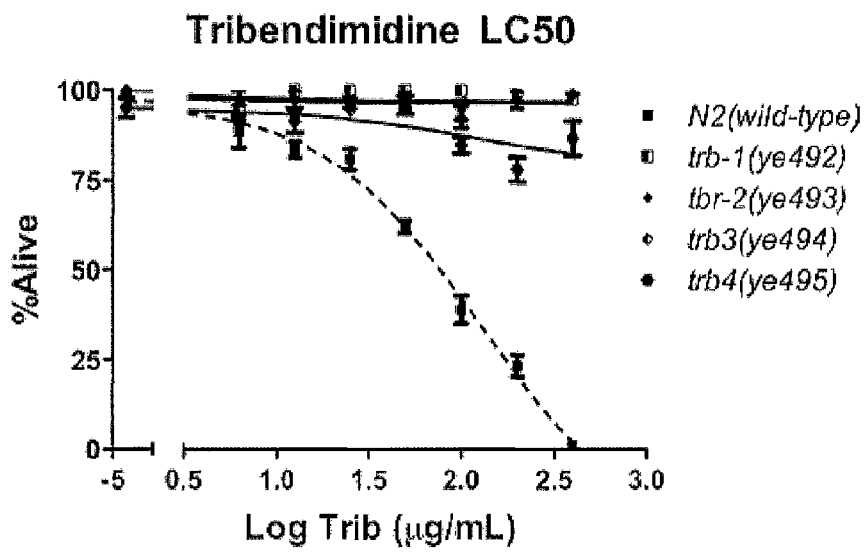
FIG. 3 is a graph of the response of C. elegans trb mutants to tribendimidine as measured by the effect on viability (log Trib (μg/ml) vs. % alive).

To quantitatively demonstrate tribendimidine resistance of nematodes mutant in each of the trb genes, we performed LC50 assays as described previously on five strains: wild-type (N2), trb-1(ye492) mutant nematodes, trb-2(ye493) mutant nematodes, trb-3(ye494) mutant nematodes, and trb4 (ye495) mutant nematodes. In addition, since trb-4(ye495) nematodes grow a little slower than the other strains, nematodes from this mutant were allowed to grow for 48 hours to allow them to progress from the L1 to the L4 stage (as opposed to 44 hours for the other four strains). As shown in FIG. 3, nematodes mutant in any one of the four trb genes were resistant to tribendimidine because at tribendimidine concentrations where most or all of the wild-type nematodes were dead (e.g., 100 µg/ml and greater), the trb-mutant nematodes were mostly or all alive. A gene mutation can be operationally defined as giving rise to resistant nematodes if ≥25% of the nematodes mutated for that gene are alive at a dose that normally kills ≥90% of *C. elegans*. An LC50 value for the trb mutants was not able to be calculated because there was no concentration in this experiment at which ≥50% of any trb mutant nematodes died.

Cross-Resistance Between Tribendimidine and Levamisole/Pyrantel

*C. elegans* mutants that are resistant to tribendimidine were also found to be resistant to levamisole. Levamisole resistance of nematodes mutant was quantitatively demonstrated in three different genes, trb-1, trb-2, and trb-4, using an LC50 assay. The trb mutant nematodes were isolated in the forward genetic screen for tribendimidine resistance described above. The LC50 assay was performed as previously described. A levamisole stock solution (100 mM stock) was prepared in water. Dilutions (2-fold) were made in SS Media accordingly such that 20 µl aliquots were added per well to give rise to the desired concentration.

Figure 4:
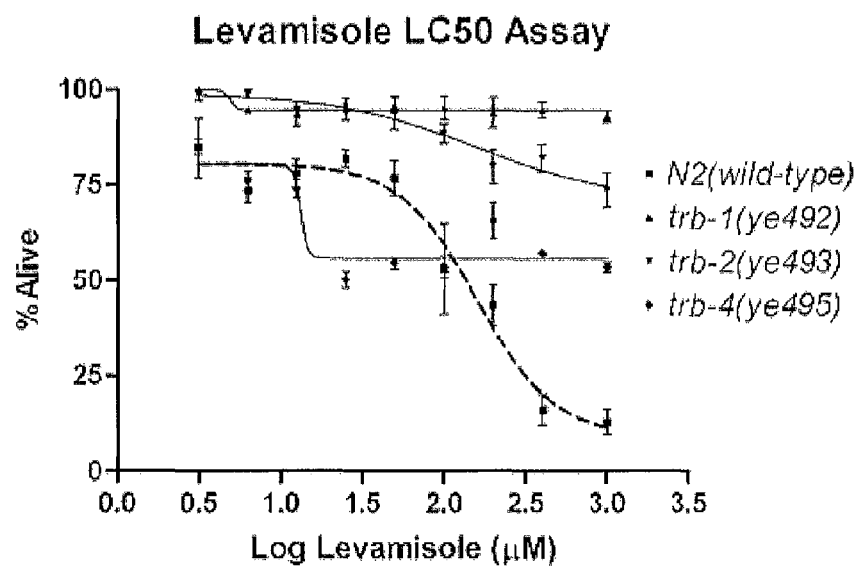
FIG. 4 is a graph of the response of C. elegans trb mutants to levamisole as measured by the effect on viability (log Lev (μg/ml) vs. % alive).

As shown in these experiments, nematodes mutant in the three trb genes were resistant to levamisole. As seen in FIG. 4, at levamisole concentrations where most or all of the wild-type nematodes were dead (1000 µM or greater), the trb mutant nematodes were mostly or all alive. Therefore, all three of the trb mutants can be classified as resistant. Note, at some lower concentrations trb-4 nematodes were more affected by levamisole than wild-type nematodes. This is probably due to the fact that trb-4 mutant nematodes were not as healthy as the other mutants even in the absence of any drug. At higher values of levamisole, it is very clear that these mutant nematodes were more resistant than wild-type nematodes. An LC50 value for the trb mutants on levamisole could not be calculated. trb-3 mutant nematodes were also resistant to levamisole. For instance, at 1 mM (1000 µM) levamisole, >40% of all trb-3(ye494) nematodes were alive (similar to trb-4).

*C. elegans* mutants that are resistant to levamisole were also found to be resistant to tribendimidine. Other laboratories over the years have identified at least 11 genes that, when mutated, give rise to *C. elegans* nematodes resistant to levamisole. (See Jones, A. K., Buckingham, S. D., and Sattelle, D. B., 2005, Chemistry-to-gene screens in *Caenorhabditis elegans*, Nat Rev Drug Discov, 4: 321-330.) We took nematodes mutated in each one of these 11 genes and performed tribendimidine LC50 assays as previously described. The only difference in protocol was that for lev-11 and unc-22 mutant nematodes, because these nematodes grow more slowly than the others, they were allowed to develop for 48 hr at 20° C. from the L1 to L4 stage before being used in the assay. Additionally, because the nematodes mutant for the other 9 genes (lev-1, lev-8, lev-9, lev-10, unc-29, unc-38, unc-50, unc-63, unc-74) grow very slightly slower, nematodes mutant in these other 9 gene were allowed to develop for 45 hours at 20° C. from the L1 to L4 stage before being used in the assay. N2 wild-type were used at 44 hours as previously described.

Figure 5:
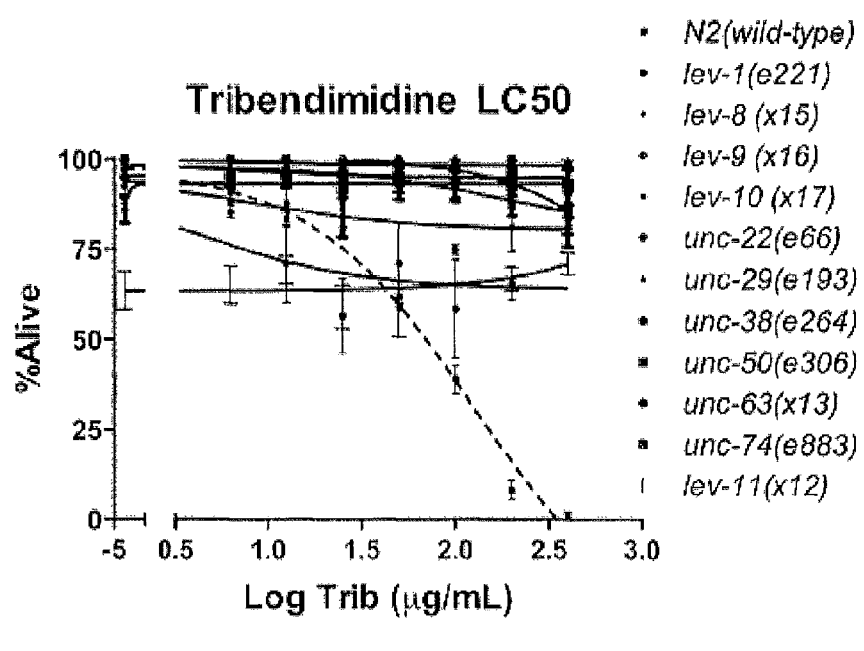
FIG. 5 is a graph of the response of C. elegans levamisole-resistant mutants to tribendimidine as measured by the effect on viability (log Trib (μg/ml) vs. % alive).

As seen in FIG. 5, nematodes mutated in any one of these eleven genes gave rise to nematodes resistant to tribendimidine. That is, at high concentrations of tribendimidine, most or all of the wild-type nematodes were dead and most of the mutant nematodes were still alive. Nematodes mutant in any one of the eleven genes passed the criterion established for resistance. Thus, nematodes with mutations in 11/11 genes tested that give rise to resistance to levamisole were also resistant to tribendimidine.

The four trb genes that mutate to tribendimidine resistance are synonymous with four of the genes that mutate to levamisole resistance. The four trb mutants were mapped onto chromosomes using traditional mapping techniques (see Marroquin et al., 2000, *Genetics*, 155: 1693-1699, which is hereby expressly incorporated by reference in its entirety). The four trb mutants trb-1, -2, -3, and -4 mapped to chromosomes I, X, III, and IV, respectively. These were then tested against all the levamisole-resistant genes on those chromosomes using complementation testing. In the complementation testing, GFP (green fluorescent protein)-labeled males were mated into levamisole-resistant mutants. These were then crossed into trb-resistant hermaphrodites. Some of the green cross-progeny were then plated onto tribendimidine plates and some onto levamisole plates. The matching of levamisole and trb genes was determined by their failure to complement and resistance of half of the cross progeny on tribendimidine and levamisole plates.

Tribendimidine plates: stock solution (4 mg/ml) in water was prepared and added into standard *C. elegans* NG agar media (2.5 ml/100 ml) to a final concentration of 100 µg/ml. The mixture was poured into 35 mm plates (4 ml/plate). The plates were stored up to one week at 4° C. The plates were spread with OP50, a laboratory strain of *E. coli* commonly used as a food source for *C. elegans*. Resistant=good health and motility; susceptible=contracted, pale color, move slowly.

Levamisole plates: stock solution (4 mg/ml) in water was prepared and added into standard *C. elegans* NG agar media (2.5 ml/100 ml) to a final concentration of 100 µg/ml. The mixture was poured into 35 mm plates (4 ml/plate). The plates were stored up to one week at 4° C. The plates were spread with OP50. Resistant=good health and motility; susceptible=contracted, pale color, move slowly.

Results of the complementation experiment are reported in TABLE 3.

TABLE 3

| Tribendimidine (trb) resistance genes | Levamisole (lev) resistance genes |
|---|---|
| trb-1 | unc-63 |
| trb-2 | lev-8 |
| trb-3 | unc-50 |
| trb-4 | unc-22 |

These results were entirely unexpected—that is that a screen for tribendimidine-resistant nematodes results in mutations in the very same genes known to be important for resistance to levamisole. These results, and the results showing that 11/11 *C. elegans* mutants resistant to levamisole are also resistant to tribendimidine, definitively show that the mechanism of action of tribendimidine is the same as levamisole.

Figure 6:
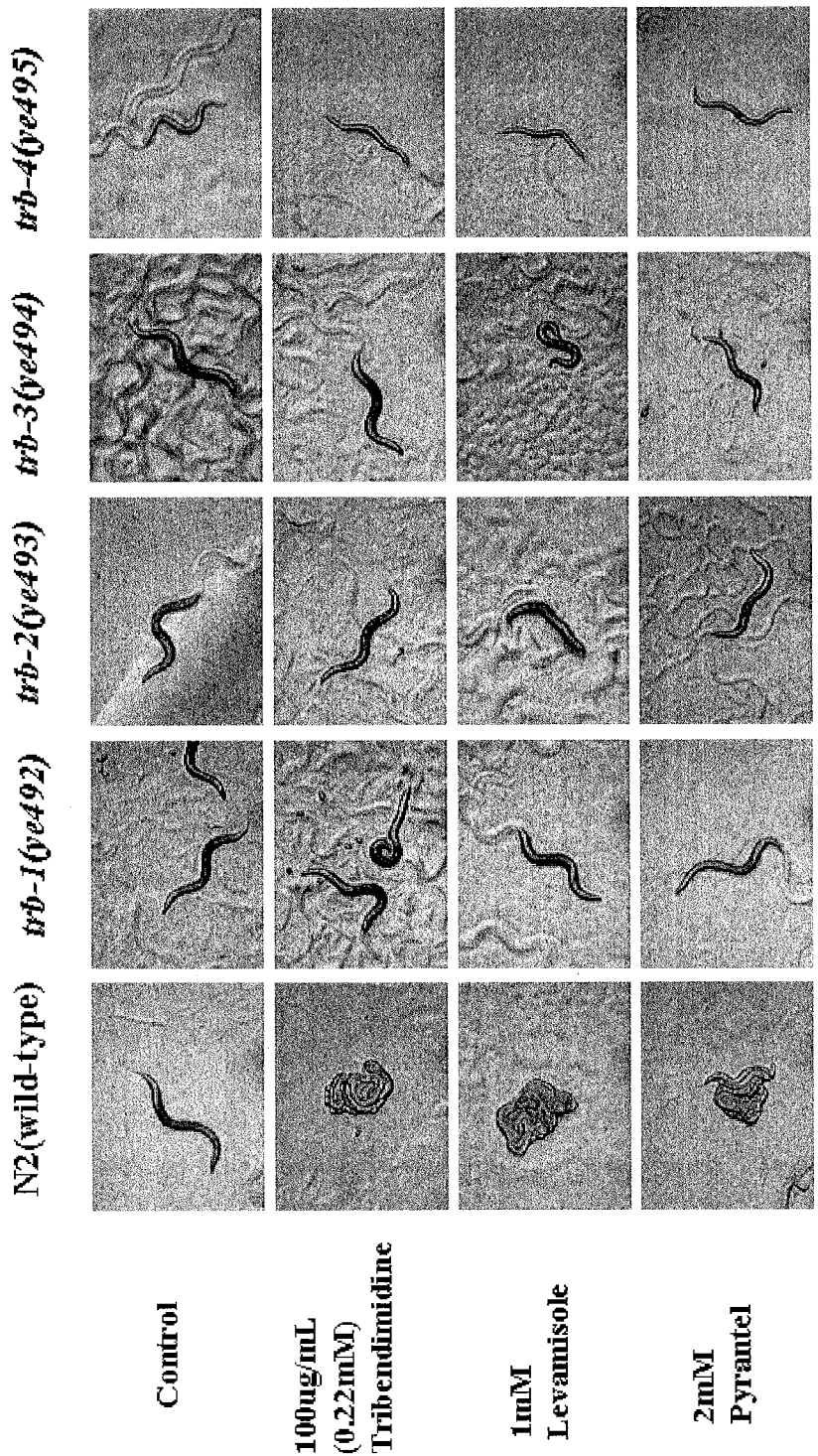
FIG. 6 are photographs of C. elegans wild-type and trb mutants on tribendimidine, levamisole, or pyrantel plates.
Figure 7:
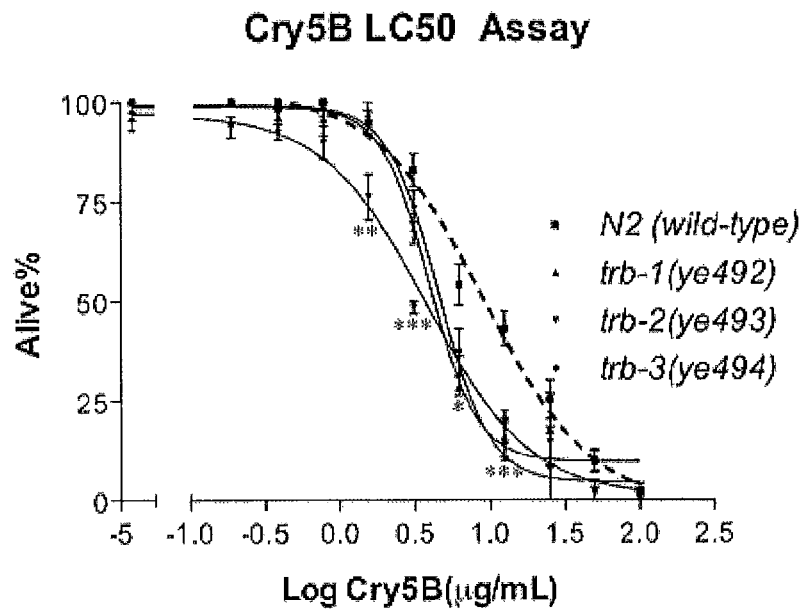
FIG. 7 is a graph of the response of C. elegans wild-type and trb mutants to Cry5B as measured by the effect on viability (log Cry5B (μg/ml) vs. % alive).
Figure 8:
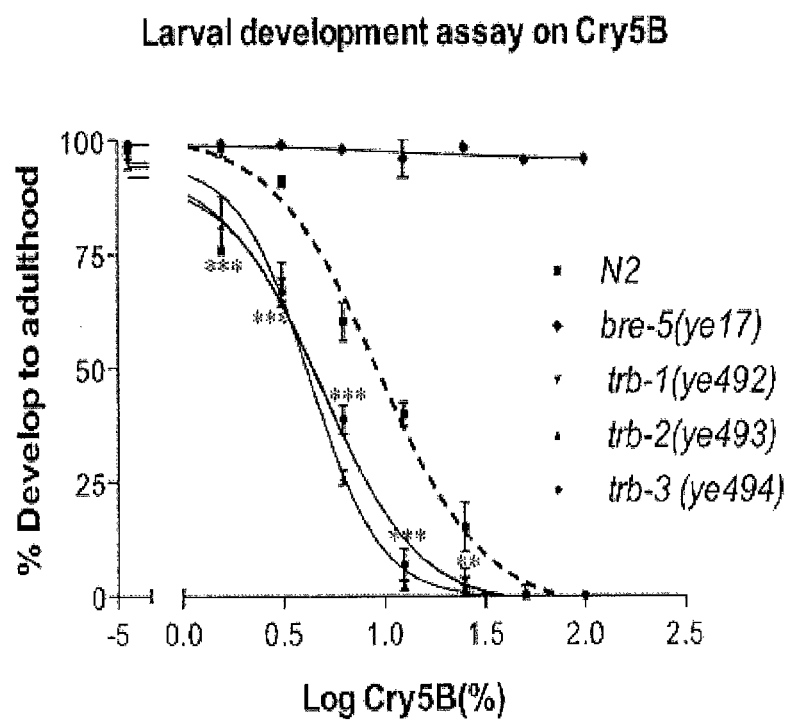
FIG. 8 is a graph of a C. elegans (wild-type and mutants) larval development assay on Cry5B (log Cry5B (μ/ml) vs. % develop to adulthood).
Figure 9:
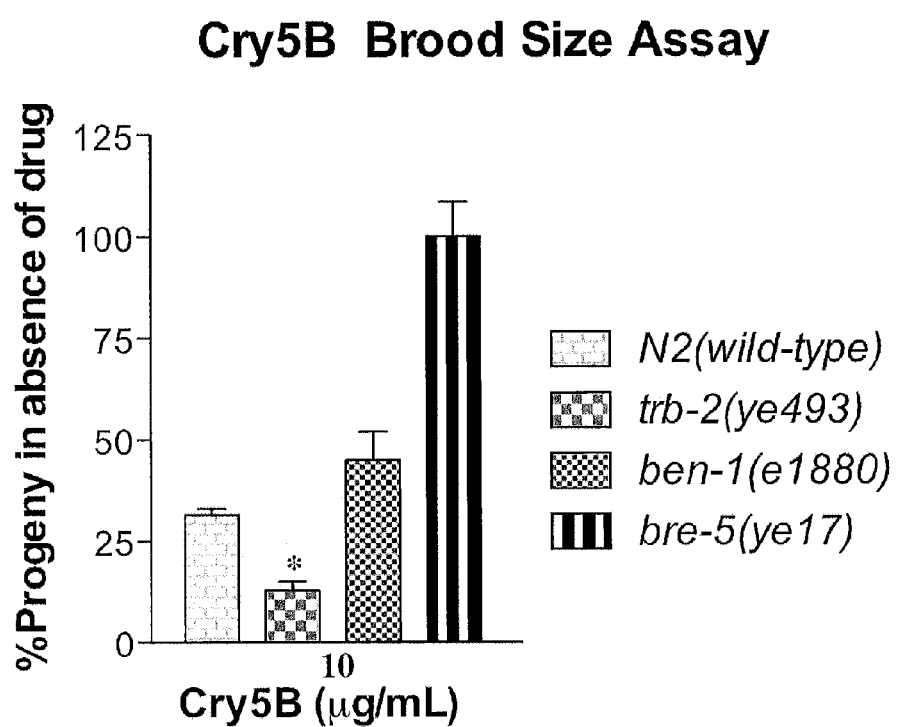
FIG. 9 is a graph of a C. elegans (wild-type and mutants) brood size assay on Cry5B (Cry5B (μg/ml) vs. % progeny in absence of drug).

Tribendimidine-resistant nematodes were also resistant to pyrantel. Pyrantel plates were prepared by preparing a pyrantel stock solution (100 mM in water) and adding the stock solution 1:50 in molten NG agar prior to pouring. As shown in FIG. 6, wild-type *C. elegans* nematodes placed onto tribendimidine, levamisole, or pyrantel plates were sick (as seen by small, pale, and immobile clumped worms). Using this visual assay, it was readily concluded that trb-1, trb-2, trb-3, and trb-4 mutant nematodes were resistant to each of tribendimidine, levamisole, and pyrantel. Therefore, in addition to our previous data that showed these mutant nematodes to be resistant to tribendimidine and levamisole, this data demonstrates that resistance also extends to pyrantel, which is an nAChR agonist already known to have the same mechanism of action as levamisole. (See Martin, R. J. and Robertson, A. P., Mode of action of levamisole and pyrantel, anthelmintic resistance, E153 and Q57, Parasitol 134: 1093-1104)

Levamisole and pyrantel are cholinomimetic anthelmintics that act as ligands (agonists) of the nicotinic acetylcholine receptor (nAChR) located on nematode muscle (Robertson and Martin, 2007, *Invert. Neurosci.*, 7:209-217, which is hereby expressly incorporated by reference in its entirety). The drugs mimic acetylcholine but unlike the native neurotransmitter are not broken down. The result is spastic paralysis of the worm. Thus, our data show that tribendimidine is, unexpectedly, an nAChR agonist. It is in the same class of nAChR agonists as levamisole and tribendimidine. Other nAChR agonists are known, e.g., an AAD drug recently developed by Novartis. (See Kaminsky et al., 2008, *Nature*, 452: 176-181, which is hereby expressly incorporated by reference in its entirety.)

Hypersusceptibility

The term hypersusceptibility comes from the HIV field. Viral isolates with reduced susceptibility or resistance to some antiretroviral drugs may exhibit significant increased susceptibility to other drugs acting on the same enzyme. This phenomenon is known as hypersusceptibility and there is growing evidence that the use of drug combinations that have this hypersusceptible relationship result in improved clinical outcomes (Zaccarelli et al., 2004, *Current HIV Research*, 2: 283-292, which is hereby expressly incorporated by reference in its entirety). Thus, hypersusceptibility is a highly desirable trait among multiple drugs in that it seems to result in improved clinical outcomes. In contrast to the HIV field in which the drugs are acting on the same enzyme, the drug combinations of the present invention do not target the same enzyme. Nonetheless, the relationship between resistance and the drugs is preserved in HIV and Cry5B/nAChR agonist.

Tribendimidine/Levamisole/Pyrantel-Resistant Mutants were Hypersusceptible to Cry5B Cry5B is an anthelmintic crystal protein (also called Cry protein or Cry toxin) made by the soil bacterium *Bacillus thuringiensis* (Bt). (Marroquin et al., Genetics 2000; Griffitts et al., Science 2001; Wei et al., PNAS 2003) Cry proteins are a large family of related proteins that have been used mostly as natural insecticides, although a few are known to kill nematodes (nematicides).

Wild-type and trb-1/unc-63, trb-2/lev-8, and trb-3/unc-50 mutant nematodes were subjected to a standard LC50 assay using Cry5B as the anthelmintic. As seen in FIG. 7, for all three of the trb mutants tested, the LC50 values were lower than for wild-type indicating they are hypersusceptible to Cry5B. In addition, the LC50 values for all three of the mutants were below the bottom of the 95% confidence limits for wild-type (N2) and the LC50 value of wild-type (N2) was above the 95% confidence limits for each of the three mutants. Therefore, the hypersusceptibility of all three of the trb mutants was statistically significant. Another way to look at the statistical significance is to compare the statistical significance of pairwise comparisons using PRIZM. For example, concentrations at which the trb-2/lev-8 mutant differed significantly from wild type are indicated by asterisks (*$p<0.05$, $p<0.01$, *$p<0.001$). This relationship between trb animals and Cry5B is unexpected—trb mutants were isolated based on their resistance to nAChR agonists that target the neuromuscular synapse. Cry5B is a pore-forming toxin that functions at the intestine. It is unknown why resistance to nAChR agonists would make worms hypersusceptible to an intestinal pore-forming toxin.

Cry5B for LC50 Assay.

Cry5B precipitate purified as in Cappello et al., 2006 from the −80° C. freezer was resuspended in 20 mM Hepes pH 8.0 at 2.4 mg/ml or 1.6 mg/ml and 2× dilutions in Hepes buffer were made such that 10 μl/well is used to give the final concentrations as indicated in FIG. 7.

The relationship between nAChR agonist-resistant mutants and Cry5B was also tested using a larval development assay. The results are shown in FIG. 8. As with the LC50 assay, for all three of the trb mutants tested (trb-1/unc-63, trb-2/lev-8, and trb-3/unc-50), the IC50 values (inhibitory concentration at which 50% of the nematodes fail to reach adulthood) were lower than for wild type (N2). In addition, the IC50 values for all three of the mutants were below the bottom of the 95% confidence limits for wild-type (N2) and the IC50 value of wild-type (N2) was above the 95% confidence limits for each of the three trb mutants. Therefore, the hypersusceptibility of all three of the trb mutants was statistically significant. The bre-5 mutant, which is known to be resistant to Cry5B, is included here to show how a fully resistant nematode behaved in these assay.

The relationship between nAChR agonist resistant mutant trb-2/lev-8 and Cry5B was also tested using a brood size assay as previously described. (L4 staged worms were used (bre-5(ye17) 45 hours old, all others 44 hours old). *C. elegans* nematodes are hermaphrodites that make both egg and sperm in a single nematode. The ability to make self-progeny (egg and sperm come from the same nematode) is dependent on the health of the nematode—if an adult hermaphrodite is sick, then it makes less progeny. We ascertained the ability of *C. elegans* wild-type and mutants to make progeny in the presence of 10 μg/ml Cry5B (normalized to the brood size of each of nematode in the absence of toxin). As shown in FIG. 9, trb-2/lev-8 mutant nematodes were more sensitive to the effects of Cry5B than wild-type nematodes ($P<0.05$) and ben-1 mutant nematodes (ben-1 mutant nematodes are resistant to benzimidazole class drugs, e.g., mebendazole, albendazole). This shows that resistance to one class of anthelmintic (e.g., benzimidazole) does not necessarily make nematodes hypersusceptible to another class (here Cry5B). Rather, it is a unique and unexpected relationship between Cry5B and nAChR resistant mutants. The data from FIGS. 7, 8, and 9 show that with three different assays measuring three different parameters of the nematodes' response to the anthelmintic, nematodes resistant to tribendimidine are hypersusceptible to Cry5B.

trb-2/lev-8 Mutant Worms were Hypersusceptible and Ben-1 Mutant Worms were Hyper Resistant to Cry5B To test whether the hypersusceptibility of tribendimidine-resistant mutants also extended to another major class of anthelmintics, e.g., the benzimidazoles, LC50 and developmental assays were performed as previously described comparing wild type, trb-2/lev-8 mutant nematodes, and ben-1 mutant nematodes on Cry5B. As seen in FIG. 10A, the trb-2 mutant has a lower LC50 value (4.236 μg/ml) than wild-type (N2) (6.920 μg/ml). Similarly in FIG. 10B, the trb-2 mutants had a lower IC50 value (3.236 μg/ml) than wild-type (N2) (7.54 μg/ml. These results confirm previous findings that tribendimidine-resistant animals were hypersusceptible to Cry5B.

In the same experiments, however, benzimidazole resistant animals (ben-1(e1880) were not hypersusceptible to Cry5B. Similar to our results in our brood size assay (see FIG. 9), ben-1 mutant nematodes were found to be hyper-resistant to Cry5B relative to wild-type (N2) nematodes. For example, in the LC50 assay (see FIG. 10A), the LC50 value for ben-1 mutant nematodes (12.53 μg/ml) was above the 95% confidence limits for N2 nematodes (5.971-8.150) and the LC50 value for wild-type (N2) nematodes (6.920 μg/ml) was below the 95% confidence limits for ben-1 mutant nematodes (10.235-15.358). Similarly, as seen in the results of the larval development assay in FIG. 10B, the IC50 value of the ben-1 mutants (8.453 μg/ml) is higher than for wild type (N2) (7.54 μg/ml). This confirms the fact that resistance to one class of anthelmintic (here benzimidazoles) does not necessarily make the nematodes hypersusceptible to another class (here Cry5B). These results reinforce the unique and unexpected relationship between nAChR resistance, which includes levamisole, pyrantel, and tribendimidine resistance, to Cry5B.

trb-2 Nematodes were Hypersensitive to Other Cry Proteins

Figure 11A:
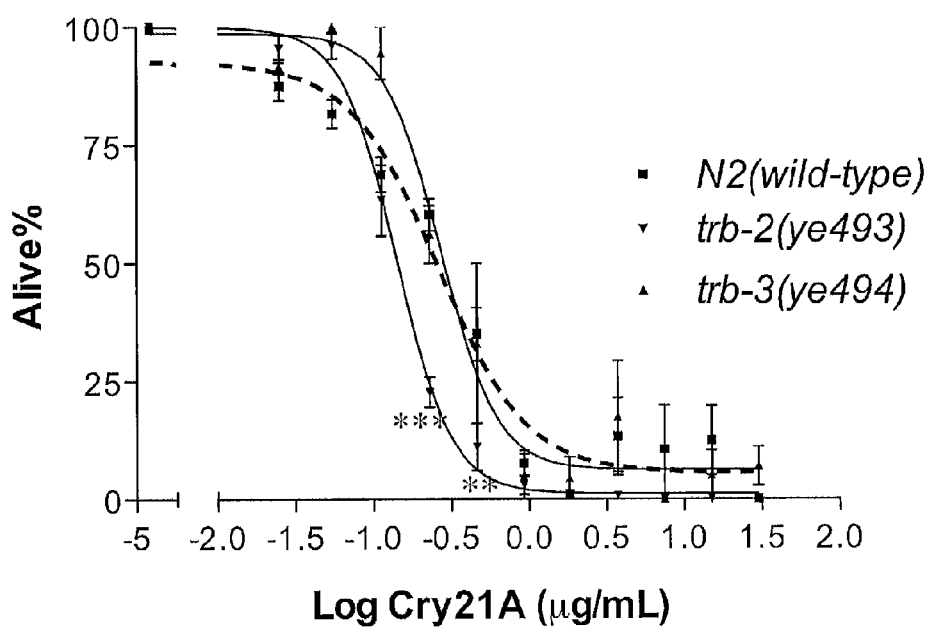
FIG. 11A is a graph of the response of C. elegans wild-type and trb mutants to Cry21A as measured by the effect on viability (log Cry21A (μ/ml) vs. % alive).

Cry5B, like all three-domain Cry proteins, is a pore-forming toxin. There are other Cry proteins that can kill nematodes, like Cry21A, Cry14A, Cry13A, and Cry6A (Wei et al., 2003, *PNAS*; Marroquin et al., 2000, *Genetics*; Griffins et al., 2001, Science; Kotze A. C., et al., 2005, *Int J Parasitol*, 35: 1013-1022; Cry6A is a non-three-domain Cry protein that has pore-forming activity; Dr. Jean-Louis Schwartz, personal communication). Cry13A, Cry14A, and Cry21A are all predicted to be three domain proteins that are part of the Cry5B branch of the Cry protein family (de Maagd, R. A., et al., 2001, *Trend Genet*; Wei et al., 2003, PNAS) As seen in FIGS. 11A and B, trb-2 and trb-3 mutant nematodes were tested on Cry21A and Cry6A LC50 assays, respectively. trb-2 mutant nematodes were found to be hypersusceptible to Cry21A and Cry6A. The LC50 values for trb-2 mutants for Cry21A (0.387 μg/ml) and Cry6A (7.017 μg/ml) were less than the values for wild-type (N2) for Cry21A (0.676 μg/ml) and Cry6A (19.917 μg/ml). A difference between trb-3 mutants and wild-type (N2) is not easy to discern in response to Cry21A and Cry6A. Although the LC50 of Cry21A for trb-3 mutants was lower than for N2 wild type (0.385 μg/ml vs. 0.676 μg/ml), the shapes of the dose-response curves do not readily suggest hypersusceptibility. The LC50 for trb-3 mutants for Cry6A was not statistically different than that of N2 wild type (23.819 μg/ml vs. 19.917 μg/ml). This result shows that some nAChR agonist (lev/pyr/trib class) resistant mutants (e.g., trb-2) are hypersensitive to likely all Cry proteins (and likely all pore-forming toxins). Thus for some cases where resistance to the lev/pyr/trib class anthelmintic has developed, Cry proteins in general are likely to be an excellent choice for anthelmintic.

Cry5B-Resistant Worms are Hypersusceptible to Tribendimidine

Figure 10A:
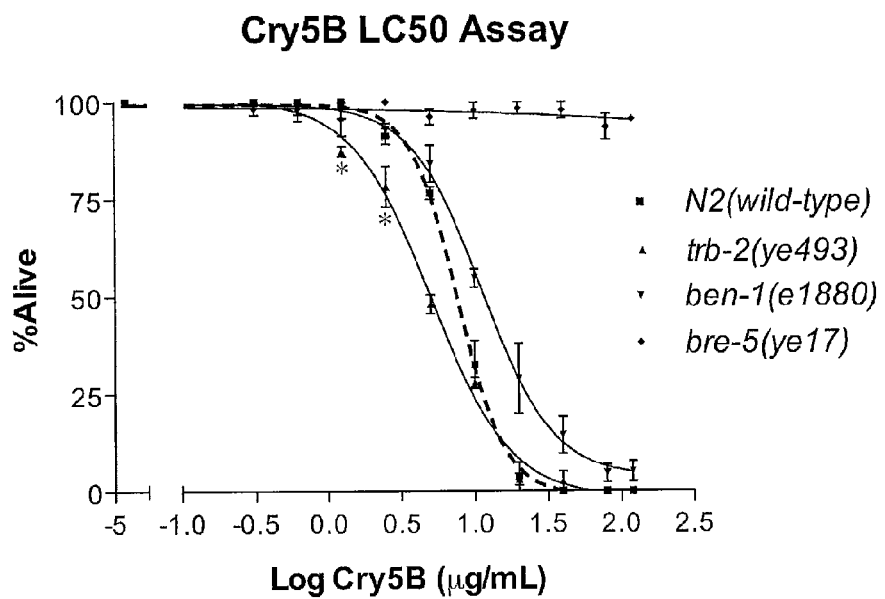
FIG. 10A is a graph of the response of C. elegans wild-type and mutants to Cry5B as measured by the effect on viability (log Cry5B (μg/ml) vs. % alive).
Figure 10B:
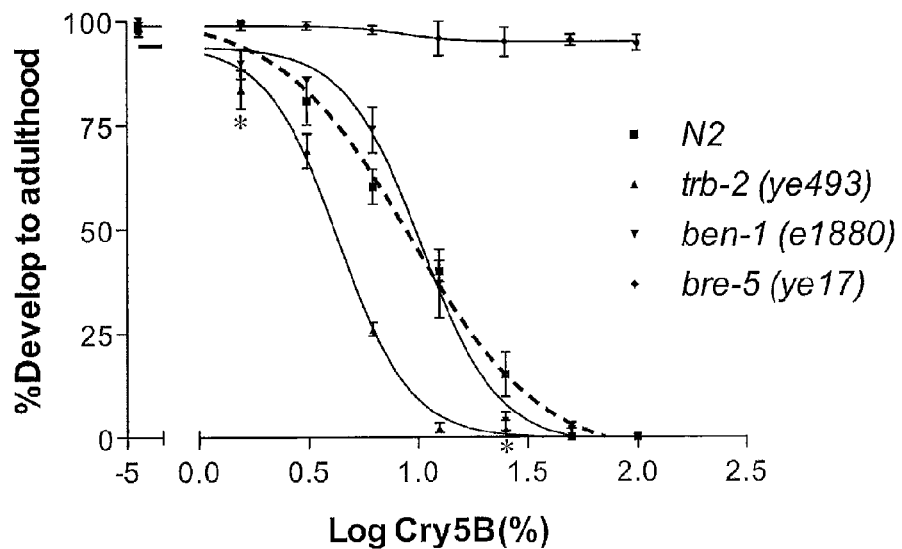
FIG. 10B is a graph of a C. elegans (wild-type and mutants) larval development assay on Cry5B (log Cry5B (μg/ml) vs. % develop to adulthood).
Figure 11B:
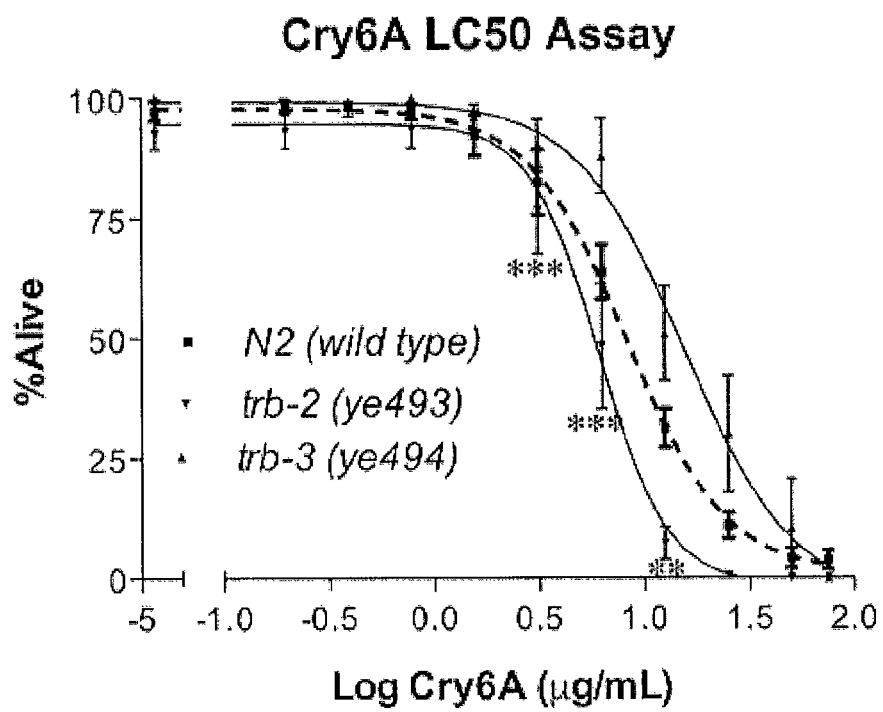
FIG. 11B is a graph of the response of C. elegans wild-type and trb mutants to Cry6A as measured by the effect on viability (log Cry6A (μg/ml) vs. % alive).
Figure 12:
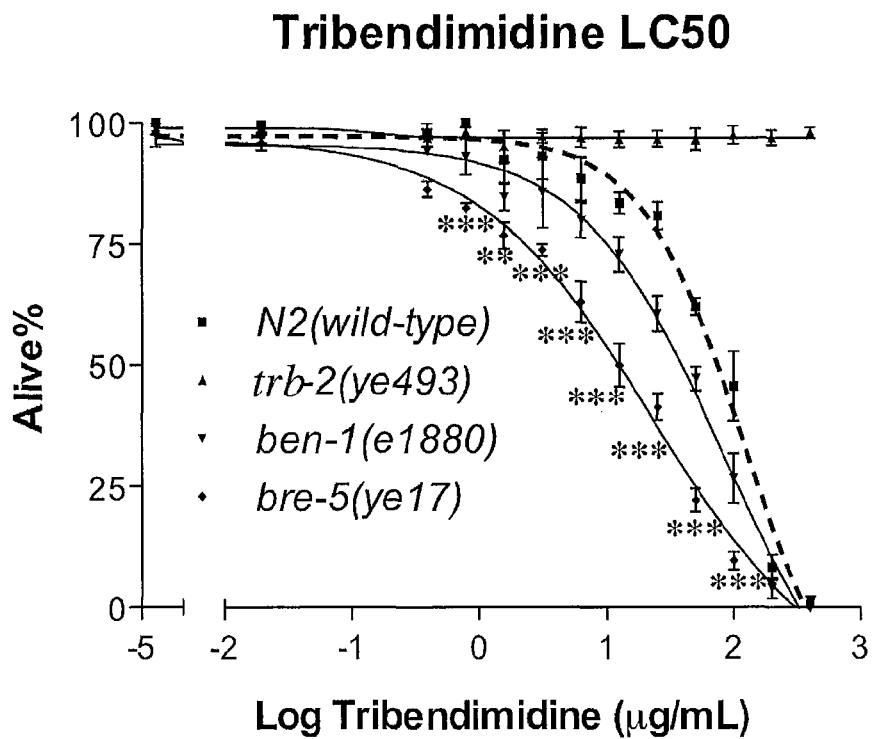
FIG. 12 is a graph of the response of C. elegans wild-type and mutants to tribendimidine as measured by the effect on viability (log Trib (μ/ml) vs. % alive).

Nematodes resistant to the nAChR agonists of the lev/pyr/trib class were shown to be hypersusceptible to Cry5B (see FIGS. 10-11). In order to determine if the reverse is true, i.e., whether nematodes resistant to Cry5B are hypersusceptible to nAChR agonists of the lev/pyr/trib class of nAChR agonists, Cry5B-resistant nematodes (genotype bre-5(ye17)) were tested in a tribendimidine LC50 assay. As seen in FIG. 12, the LC50 value for the Cry5B mutants (bre-5) (12.3 μg/ml) was significantly lower than the LC50 value for wild-type (N2) (58.372 μg/ml). Therefore, the Cry5B-resistant mutant bre-5 was found to be hypersusceptible to tribendimidine relative to wild-type nematodes. Note, trb-2 mutant nematodes were fully resistant in this assay (as predicted) and one cannot calculate an LC50 at these doses.

The response of Cry5B (bre-5)-mutant nematodes to tribendimidine was also compared with the response of wild-type nematodes in a standard larval development assay. (See FIG. 13) The IC50 values for wild-type (N2) and Cry5B (bre-5 (ye17)) mutants were 14.718 μg/ml and 13.150 μg/ml, respectively. Although the IC50s between wild-type (N2) and bre-5 (ye17) mutants were not statistically different, dose ranges of tribendimidine could be identified, e.g., 6.25 μg/ml to about 12.5 μg/ml, in which Cry5B (bre-5)-mutant nematodes were significantly more sensitive than wild-type animals to tribendimidine (see *, ** data points where * means P<0.05 and ** means P<0.01).

A brood size assay was also carried out for wild-type (N2), benzimidazole-resistant (ben-1), and Cry5B-resistant (bre-5) mutant nematodes on tribendimidine. As shown in FIG. 14, Cry5B-resistant (bre-5) mutant nematodes were hypersusceptible to tribendimidine based on brood size. That is, the brood size of Cry5B-resistant (bre-5) mutant nematodes were reduced significantly (P<0.01) relative to wild-type nematodes in the presence of 200 μg/ml of tribendimidine. Combined with the data in FIGS. 12 and 13, it is apparent that Cry5B-resistant (bre-5) mutant nematodes are definitively hypersusceptible to tribendimidine.

Figure 13:
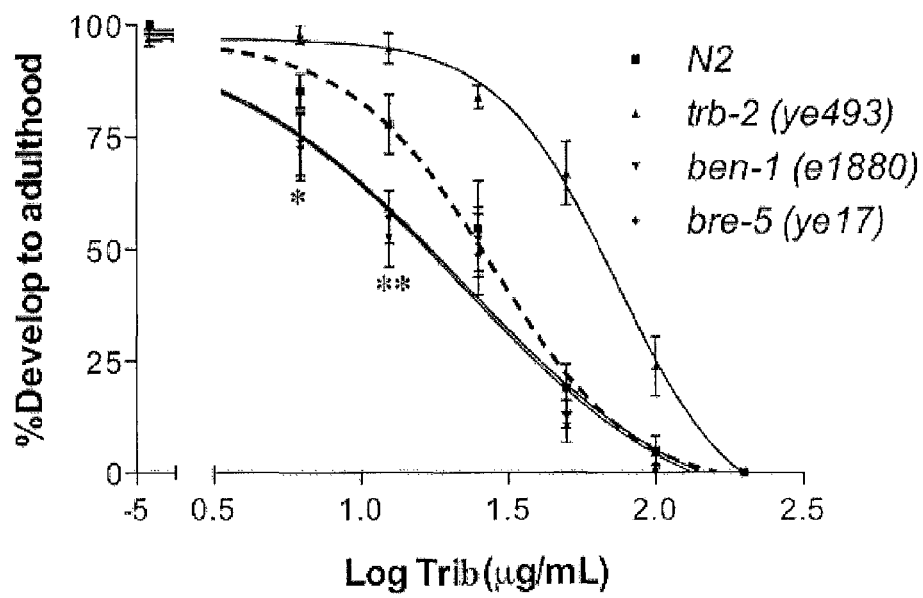
FIG. 13 is a graph of a C. elegans (wild-type and mutants) larval development assay on tribendimidine (log Trib (μg/ml) vs. % develop to adulthood).
Figure 14:
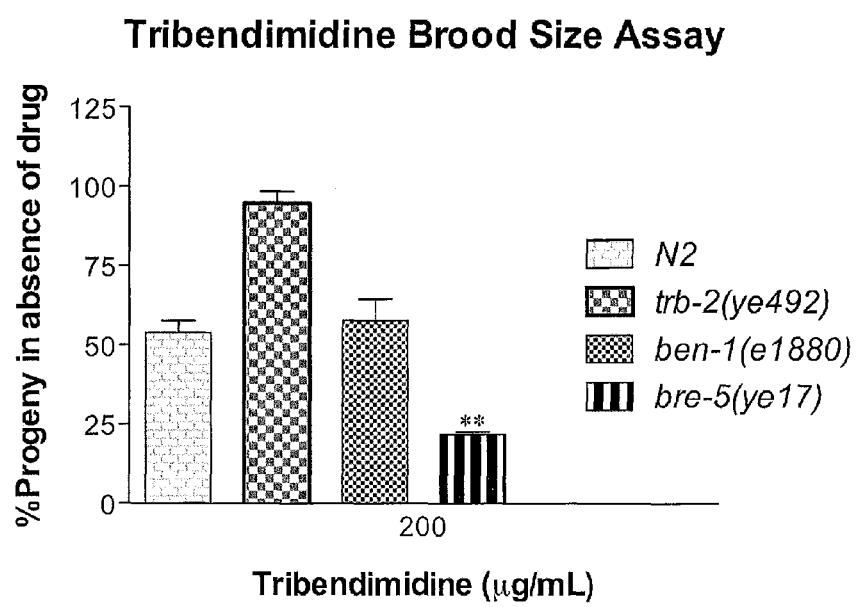
FIG. 14 is a graph of a C. elegans (wild-type and mutants) brood size assay on tribendimidine (tribendimidine (μg/ml) vs. % progeny in absence of drug).
Figure 15A:
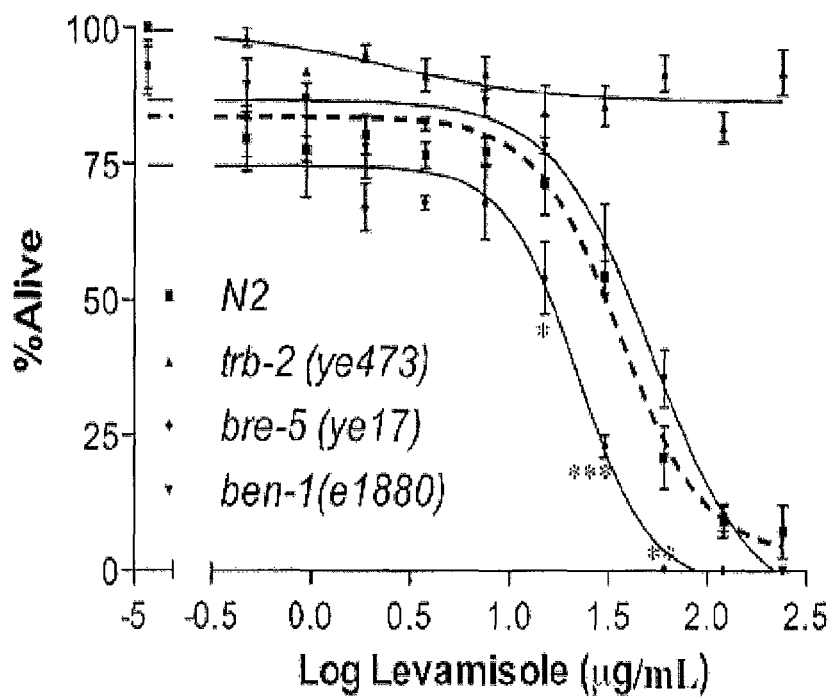
FIG. 15A is a graph of the response of C. elegans wild-type and mutants to levamisole as measured by the effect on viability (log levamisole (μg/ml) vs. % alive).
Figure 15B:
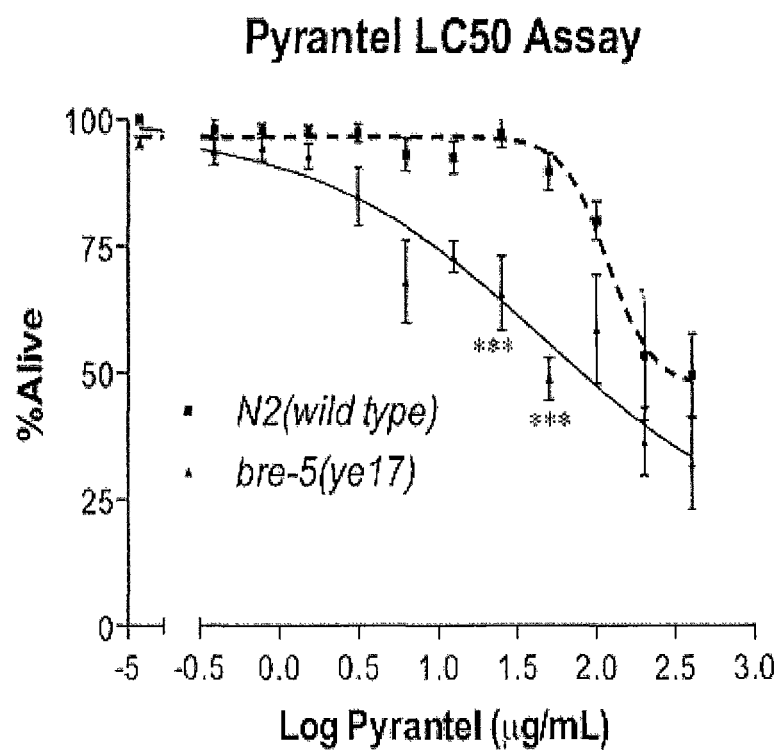
FIG. 15B is a graph of the response of C. elegans wild-type and mutants to pyrantel as measured by the effect on viability (log pyrantel (μg/ml) vs. % alive).

Cry5B-Resistant Worms are Hypersusceptible to Levamisole and Pyrantel bre-5 mutant nematodes, selected based on their resistance to Cry5B, have been shown to be hypersusceptible to tribendimidine (see FIGS. 12-14). Because levamisole and pyrantel were shown to be in the same class of anthelmintic as tribendimidine (see FIGS. 4-6), LC50 assays were performed to determine if bre-5 mutant nematodes were hypersusceptible to levamisole and pyrantel as well. As seen in FIGS. 15A and B, bre-5 (ye17) nematodes were subjected to a standard LC50 assay in levamisole and pyrantel and were found to be hypersusceptible to both drugs. The LC50 value for bre-5 mutant nematodes (9.99 μg/ml) was significantly less than the LC50 value wild-type (N2) nematodes (19.621 μg/ml) in the levamisole assay. (See FIG. 15A) Similarly in the pyrantel assay, the LC50 value for bre-5 mutant nematodes (114.144 μg/ml) was significantly less than the LC50 value wild-type (N2) nematodes (502.284 μg/ml). (See FIG. 15B)

Cry5B-Resistant Worms bre-5 Nematodes were also Resistant to Cry21A and Cry14A

Figure 16:
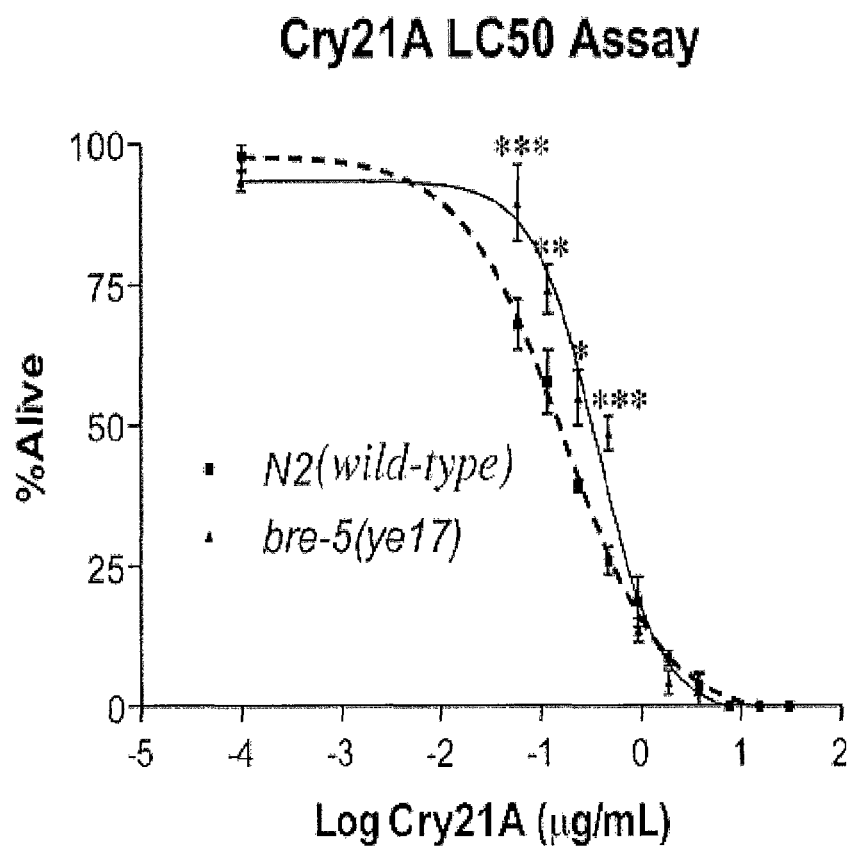
FIG. 16 is a graph of the response of C. elegans wild-type and bre-5 mutants to Cry21A as measured by the effect on viability (log Cry21A (μg/ml) vs. % alive).
Figure 17A:
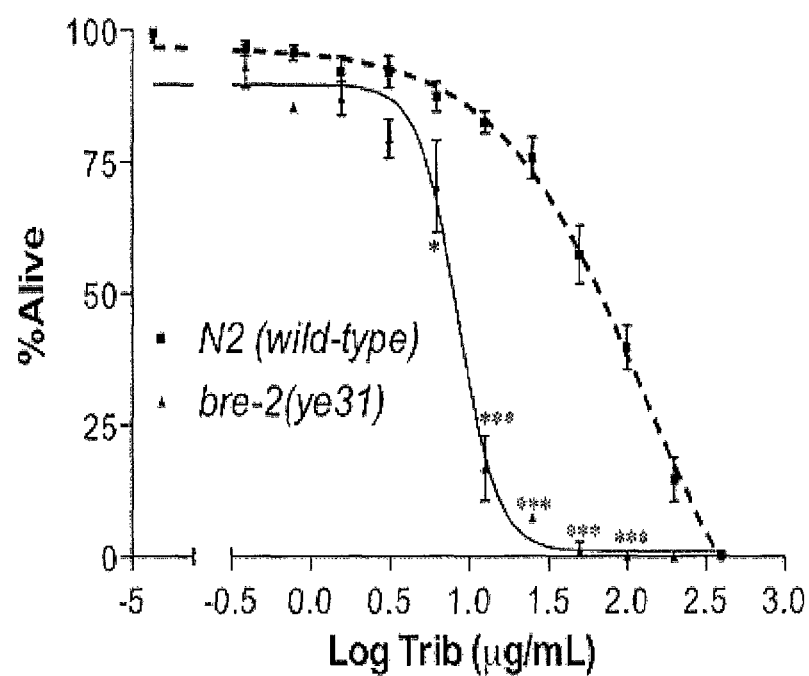
FIG. 17A is a graph of the response of C. elegans wild-type and bre-2 mutants to tribendimidine as measured by the effect on viability (log tribendimidine (μg/ml) vs. % alive).
Figure 17B:
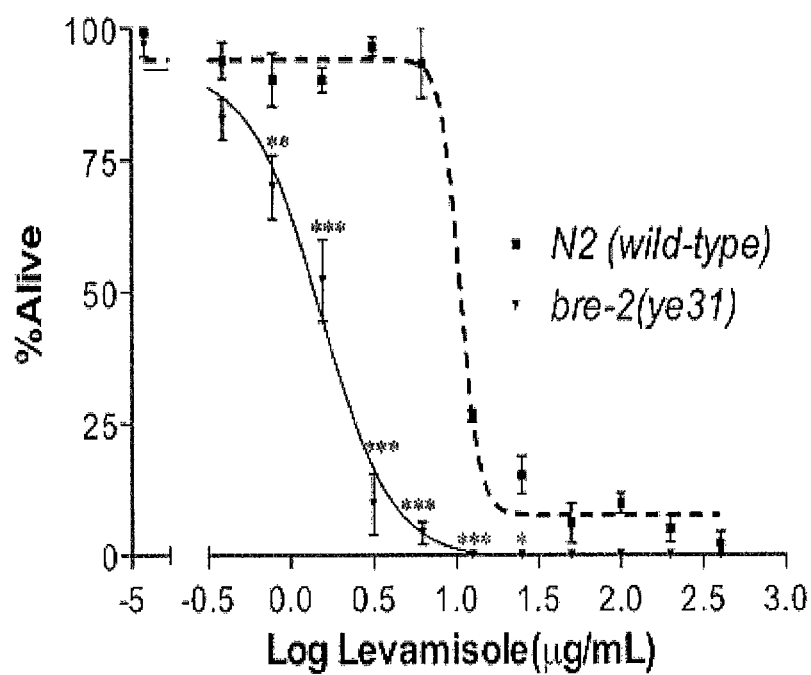
FIG. 17B is a graph of the response of C. elegans wild-type and bre-2 mutants to levamisole as measured by the effect on viability (log levamisole (μg/ml) vs. % alive).
Figure 17C:
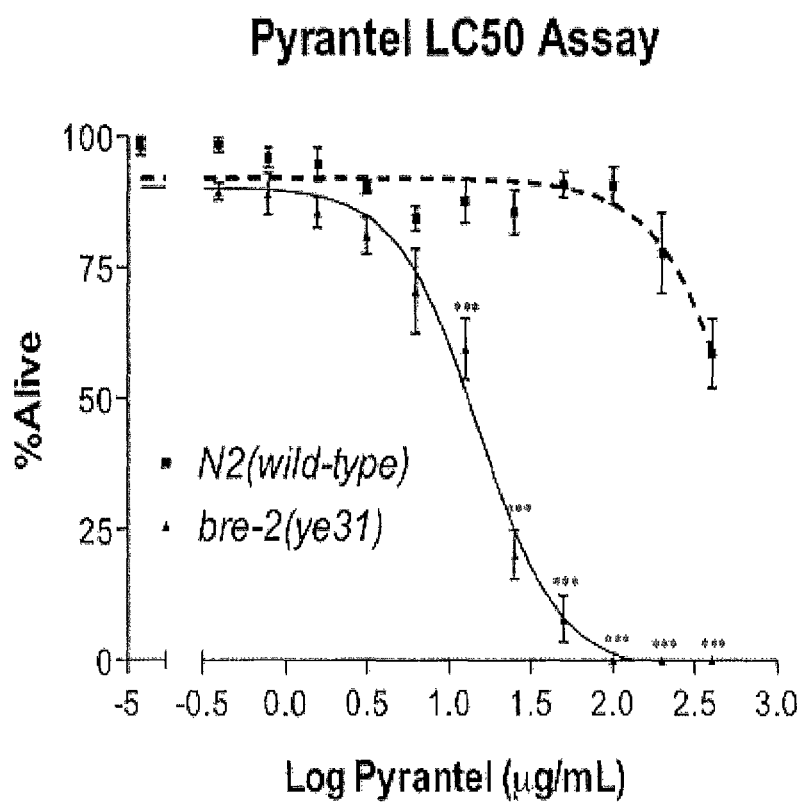
FIG. 17C is a graph of the response of C. elegans wild-type and bre-2 mutants to pyrantel as measured by the effect on viability (log pyrantel (μg/ml) vs. % alive).

Cry5B-resistant nematodes (including bre-5 mutant nematodes) have previously been reported to be resistant to the nematicidal crystal protein Cry14A, which has 34% amino acid identity to Cry5B in the toxin domain (Griffitts et al., 2001, *Science* 293:860-864; Griffitts et al., 2003, *J Biol Chem* 278: 45594-45602). LC50 assays were performed to determine if bre-5 mutant nematodes were resistant to Cry21A as well. Cry21A has 41% and 32% amino acid identity to Cry5B and Cry14A, respectively, in the toxin domain. As seen in FIG. 16, bre-5 mutant nematodes were also resistant to Cry21A. The LC50 value for bre-5 (0.300 μg/ml) was higher than the value for wild-type (N2) (0.148 μg/ml). Thus, bre-5 mutant nematodes were resistant to Cry5B, Cry14A, and Cry21A and were also hypersusceptible to tribendimidine, levamisole, and pyrantel. This data conclusively demonstrates that nematodes resistant to Cry5B, Cry21A, and Cry14A are hypersusceptible to lev/pyr/trib class nAChR agonist anthelmintics. These data predict that nematicidal Cry proteins with 32% amino acid identity to Cry5B, Cry14A, or Cry21A in their toxin domain would be good to combine with lev/pyr/trib class nAChR agonist anthelmintics since animals resistant to these Cry proteins are hypersusceptible to the nAChR agonists.

bre-2 Mutant Nematodes were Hypersusceptible to lev/pyr/trib Class nAChR Agonist Anthelmintics There are five mutants that can resist Cry5B—bre-1, bre-2, bre-3, bre-4, and bre-5 (Marroquin et al., 2000, *Genetics* v. 155: 1693-1699, which is hereby expressly incorporated by reference in its entirety). As shown in FIGS. 12-15, bre-5 mutant nematodes are hypersusceptible to the lev/pyr/trib class of nAChR agonists. In order to determine whether other Cry5B-resistant nematodes are also hypersusceptible, bre-2 mutant nematodes were tested against levamisole, pyrantel, and tribendimidine in standard LC50 assays. As seen in FIGS. 17A-C, bre-2-mutant nematodes were very hypersusceptible to all three nAChR agonists. The LC50 value for bre-2 mutant nematodes (7.271 µg/ml) was significantly less than the LC50 value wild-type (N2) nematodes (57.38 µg/ml) in the tribendimidine assay. (See FIG. 17A) For levamisole, the LC50 value for bre-2 mutant nematodes (1.160 µg/ml) was significantly less than the LC50 value wild-type (N2) nematodes (11.712 µg/ml). (See FIG. 17B) Similarly in the pyrantel assay, the LC50 value for bre-2 mutant nematodes (10.871 µg/ml) was significantly less than the LC50 value wild-type (N2) nematodes (594.956 µg/ml). (See FIG. 17C) Therefore, both bre-5 and bre-2 were found to be hypersusceptible to the lev/pyr/trib class of nAChR agonists. bre-2 mutant animals are known to be resistant to Cry14A (Griffitts et al., 2003). Because bre-2 is also known to be involved in the same biosynthetic pathway as bre-5 (Griffitts et al., 2005), and because bre-5 is resistant to Cry21A, it is also highly likely that bre-2 mutant animals are also resistant to Cry21A. These results with bre-2 reinforce the bre-5 results and indicate that resistance to Cry5B, Cry14A, and Cry21A (and proteins 2% amino acid identity to any one these proteins in the toxin domain) lead to hypersusceptibility to the levamisole class of anthelmintics, which include levamisole, pyrantel, and tribendimidine.

Synergy

Synergy is defined as an effect that is more than additive (Chou, 2006, *Pharmacolog Reviews*, 58: 621-681). Synergistic interactions amongst drug combinations are highly desirable and sought after since they can result in increased efficacy, decreased dosage, reduced side toxicity, and minimized development of resistance when used clinically (Chou, 2006). The two most popular methods for evaluating drug interactions in combination therapies are isobologram and combination index (CI; Zhao et al., 2004, Clinical Cancer Res 10:7994-8004). Numerous studies in both the cancer therapy field and anti-viral therapy field, where drug combinations to counter the development of drug resistance and to minimize drug doses, use the CI index to evaluate synergy. CI is based on the approach of Chou and Talalay 1984 (Adv. Enzyme Regul. 22:27-55) and relies on the median effect principle and the multiple-drug effect equation. CI can readily be calculated using the program CompuSyn (CompuSyn, Paramus, N.J.). Chou himself (Chou 2006) defines an interaction as slightly synergistic if the CI value is 0.85-0.9, moderately synergistic if the CI value is 0.7-0.85, synergistic if the CI value is 0.3-0.7, strongly synergistic if the CI value is 0.1-0.3, and very strongly synergistic if the CI value is <0.1. In cancer therapy literature, the values of CI that define synergism can vary, for example in Lin et al., 2007, Carcinogenesis 28: 2521-2529, synergism between drugs was defined as CI<1, and in Fischel et al., 2006, Preclinical Report 17: 807-813, synergism was defined as CI<0.8. Similar numbers are used in the anti-viral therapy field. For example, in Wyles et al., 2008, Antimicrob Agents Chemotherapy 52: 1862-1864, synergism was defined as CI<0.9 and in Gantlett et al., 2007, Antiviral Res 75:188-197, synergism was defined as CI<0.9. Based on these references, we define synergism as CI values of <0.9. All of the above-referenced articles are hereby expressly incorporated by reference in their entirety.

Figure 18A:
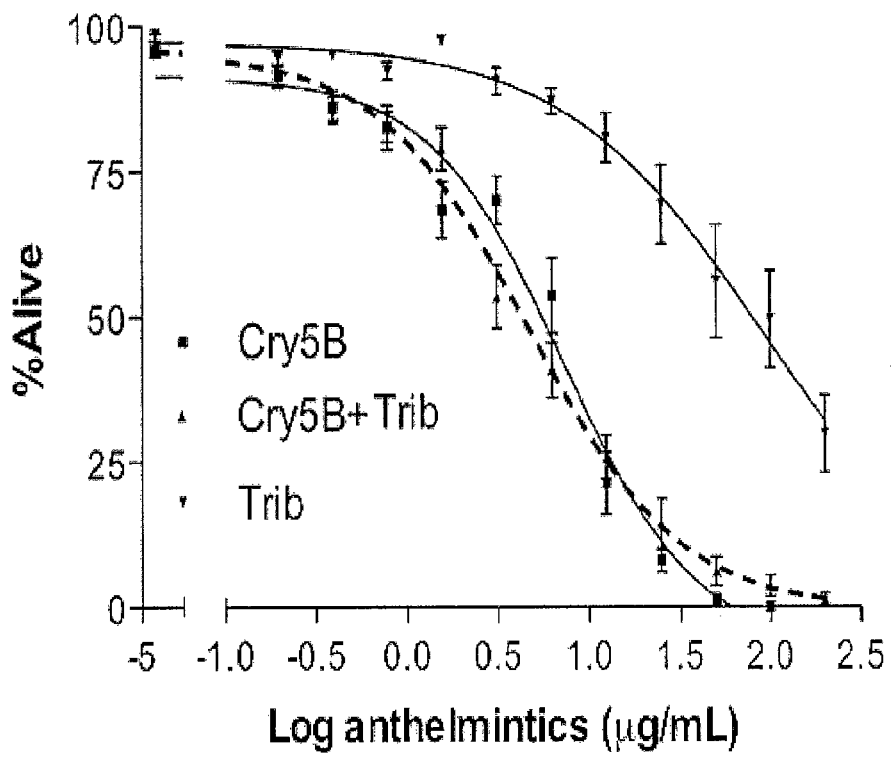
FIG. 18A is a graph of the response of wild-type C. elegans to tribendimidine and Cry5B, alone and in combination, as measured by the effect on viability (log anthelmintics (μg/ml) vs. % alive).
Figure 18B:
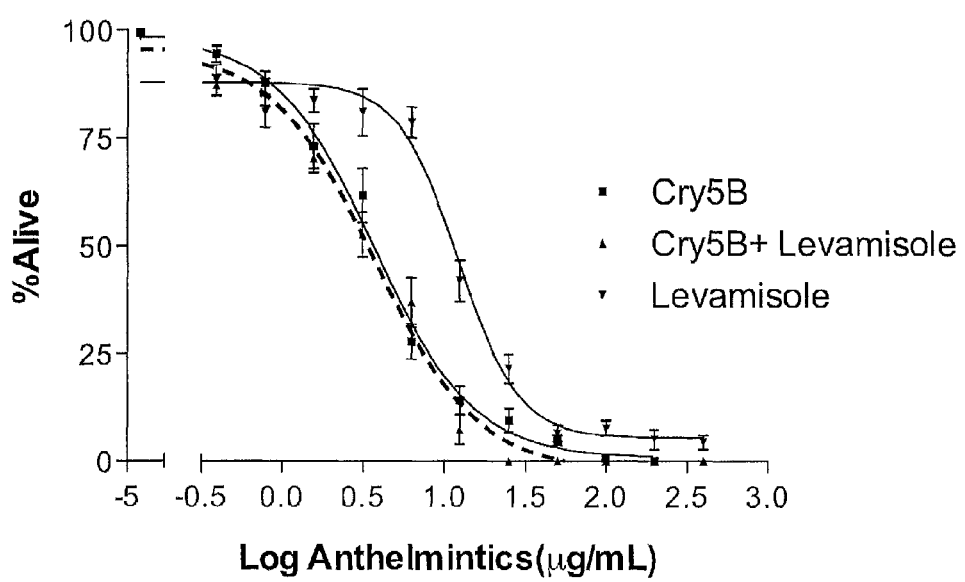
FIG. 18B is a graph of the response of wild-type C. elegans to levamisole and Cry5B, alone and in combination, as measured by the effect on viability (log anthelmintics (μg/ml) vs. % alive).
Figure 18C:
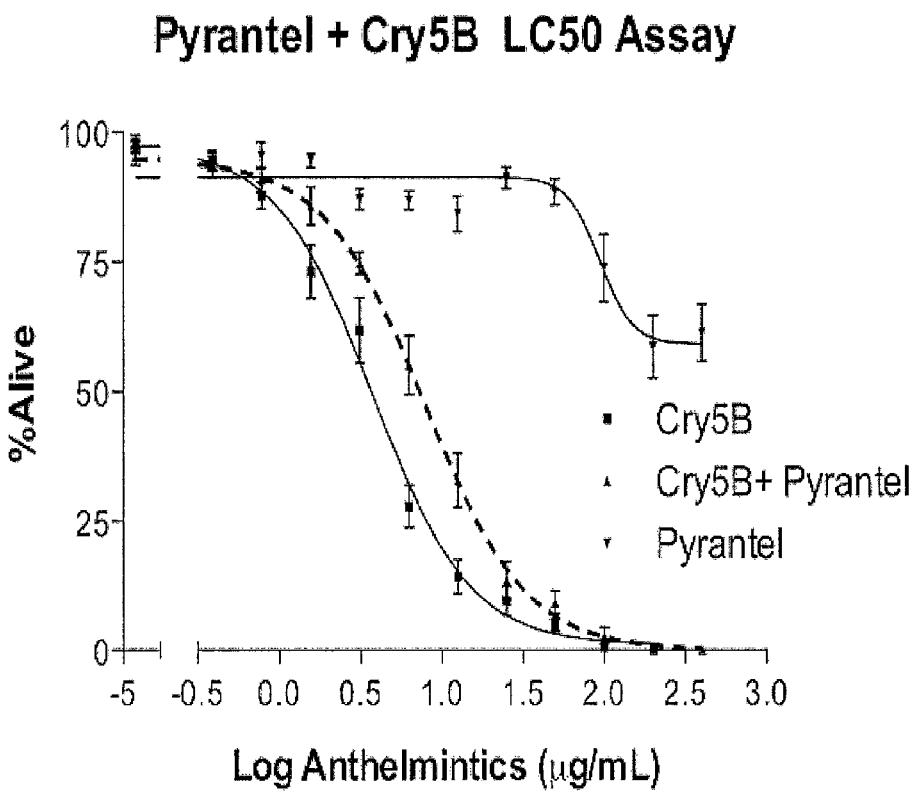
FIG. 18C is a graph of the response of wild-type C. elegans to pyrantel and Cry5B, alone and in combination, as measured by the effect on viability (log anthelmintics (μg/ml) vs. % alive).

To test for synergy between Cry5B and the lev/pyr/trib class of anthelmintics, LC50 assays were carried out on wild-type *C. elegans* nematodes using (1) Cry5B, tribendimidine, and Cry5B mixed with tribendimidine in a 1:1 ratio (based on concentration µg/ml) (see FIG. 18A); (2) Cry5B, levamisole, and Cry5B mixed with levamisole in a 1:1 ratio (based on concentration µg/ml) (see FIG. 18B); (3) Cry5B, pyrantel, and Cry5B mixed with pyrantel in a 1:1 ratio (based on concentration µg/ml) (See FIG. 18C). For each experiment, the CI value at the ED50, ED75, ED90 and ED95 (dose of drug combination that produces an effect, e.g., lethality, in 50%, 75%, 90%, and 95% of the tested population) was calculated for the drug combination. The synergism factors (CI values) for the various combinations are summarized in TABLE 4 below. In all three cases for Cry5B, the CI values were ≤0.75, showing significant synergy between Cry5B and all anthelmintics in the lev/pyr/trib nAChR agonist class. In fact, relative to levamisole and tribendimidine, the results were very impressive showing CI values≤0.41. This synergy was unexpected and unique in the anthelmintic field.

TABLE 4

|  | Cry5B | | | |
| --- | --- | --- | --- | --- |
|  | ED50 | ED75 | ED90 | ED95 |
| Trib | 0.41 | 0.28 | 0.19 | 0.14 |
| Lev | 0.39 | 0.29 | 0.22 | 0.19 |
| Pyr | 0.75 | 0.74 | 0.73 | 0.72 |

Figure 19A:
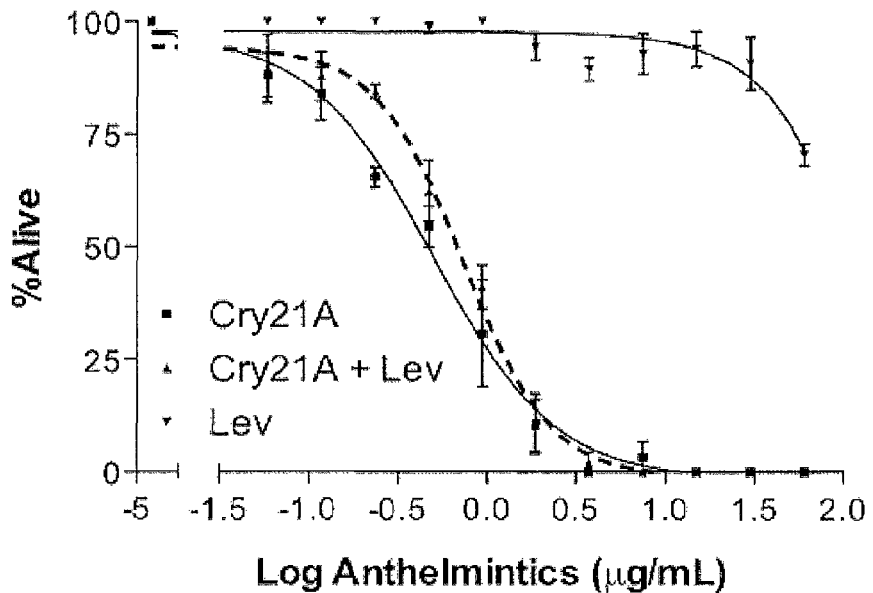
FIG. 19A is a graph of the response of wild-type C. elegans to levamisole and Cry21A, alone and in combination, as measured by the effect on viability (log anthelmintics (μg/ml) vs. % alive).
Figure 19B:
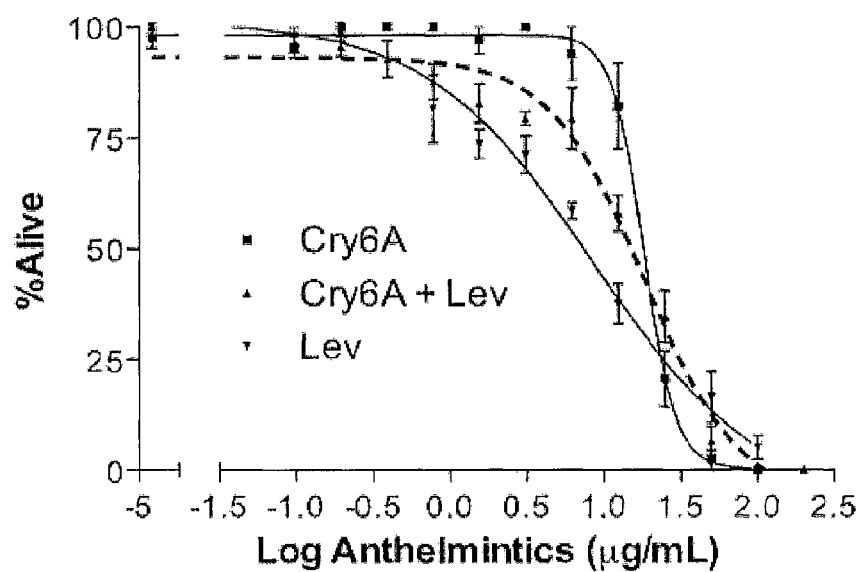
FIG. 19B is a graph of the response of wild-type C. elegans to levamisole and Cry6A, alone and in combination, as measured by the effect on viability (log anthelmintics (μ/ml) vs. % alive).

Similar experiments with Cry21A and Cry6A, each alone and in combination with levamisole were performed. As seen in FIGS. 19A-B and TABLE 5, synergism factors (CI values) of 0.63-0.37 for Cry21A and 1.14-0.82 for Cry6A were found (note, the Cry21A experiments were carried out for 3 days at 20° C., hence the lower toxicity of levamisole from previous slides. Thus, Cry21A is clearly synergistic with an nAChR agonist anthelmintic. Cry6A is synergistic at higher doses that produce the ED90 and ED95. These data show that all Cry proteins tested are able to synergize with nAChR agonist anthelmintics of the lev/pyr/trib class. Given how disparate Cry21A and Cry6A are in amino acid sequence (no significant amino acid identity), these data readily predict that all nematicidal Cry proteins will synergize with nAChR agonist anthelmintics, at least at high effect doses (ED90 and above). Given that Cry5B and Cry21A are both clearly synergistic with nAChR agonist anthelmintics at all effected ranges calculated, these data readily predict that all nematicidal Cry proteins that are phylogenetically related to Cry5B and Cry21A (see TABLE 6 below) will synergize with nAChR agonist anthelmintics at dose ranges at or above the ED50.

TABLE 5

|  | Cry21A | | | | Cry6A | | | | Cry14A | | | |
| --- | --- | --- | --- | --- | --- | --- | --- | --- | --- | --- | --- | --- |
|  | ED50 | ED75 | ED90 | ED95 | ED50 | ED75 | ED90 | ED95 | ED50 | ED75 | ED90 | ED95 |
| Lev | 0.63 | 0.52 | 0.42 | 0.37 | 1.14 | 0.96 | 0.86 | 0.82 | 0.75 | 0.60 | 0.50 | 0.44 |

Figure 19C:
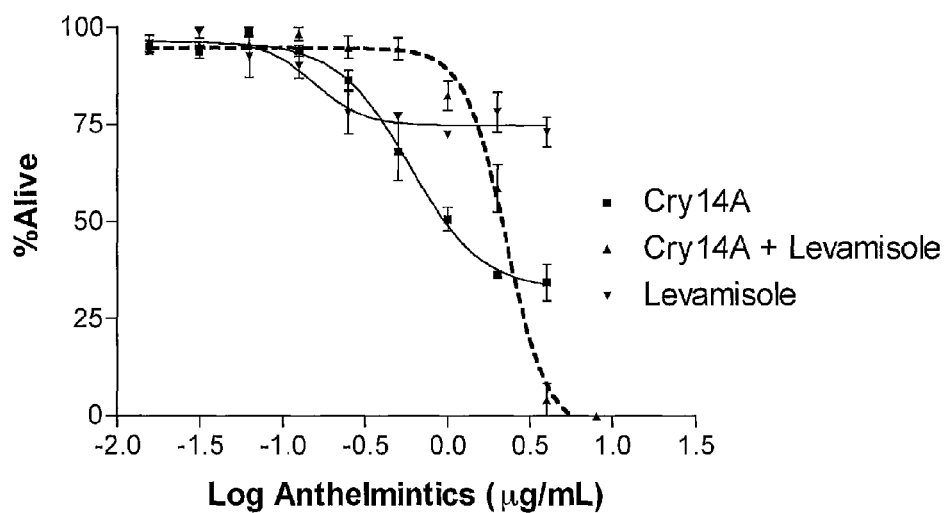
FIG. 19C is a graph of the response of wild-type C. elegans to levamisole and Cry14A, alone and in combination, as measured by the effect on viability (log anthelmintics (μg/ml) vs. % alive).
Figure 19D:
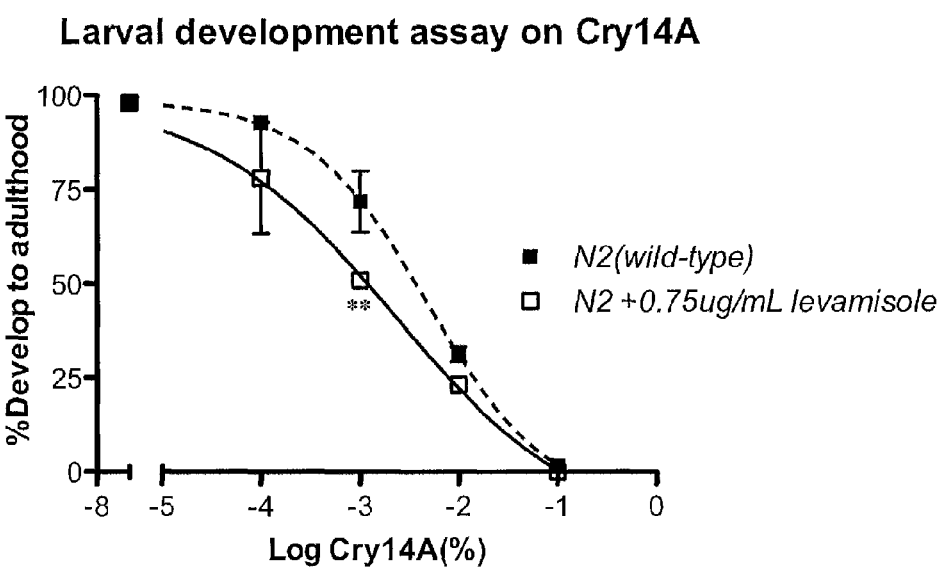
FIG. 19D is a graph of the response of wild-type C. elegans to Cry14A, alone and in combination with a low dose of levamisole, as measured by the effect on larval development (log Cry14A(%) vs. % Develop to adulthood).

Similar experiments with a strain that produces Cry14A, alone and in combination with levamisole were performed. As seen in FIG. 19C and TABLE 5, CI values at the ED50, ED75, ED90, and ED95 of 0.75, 0.60, 0.50, and 0.44, respectively, were found. The Bt strain used in these experiments expressed Cry14A and two insecticidal Cry proteins (Cry34A and Cry35A) that are not expected to affect nematodes. It is therefore predicted that the active synergistic component with levamisole is Cry14A. To confirm this conclusion, an independent test of synergy between levamisole and Cry14A was carried out. In these experiments, N2 wild-type worms were plated onto Cry14A plates+/−levamisole. A very small dose of levamisole (0.75 μg/ml), which normally does not inhibit worm development, was added to the Cry14A plates. This small dose of levamisole was found to increases the effectiveness at which Cry14A inhibits *C. elegans* development in our standard developmental assay (see FIG. 19D). In particular, at the dose of 0.1% Cry14A, there was a statistically significant drop in the viability of *C. elegans* in the presence of this low levamisole dose relative to the viability of *C. elegans* on 0.001% Cry14A alone. Thus, Cry14A alone is sufficient to synergize with levamisole, and it is highly probable that the synergy seen in FIG. 19C is due to Cry14A. These results support the conclusions all nematidical Cry proteins and all nematicidal Cry proteins phylogenetically related to Cry5B, Cry21A, and Cry14A synergize with nAChR agonist anthelmintics (see TABLE 6 below).

Cry14A Dose Response Plates.

The Cry14A gene was cloned in the pQE9 expression vector and transformed into *E. coli* JM103 (Wei et al., 2003, PNAS). Control bacteria were JM103 bacteria transformed with empty pQE9 vector. A colony of each of the bacterial strains were grown overnight in LB media supplemented with carbenicillin (50 μg/mL) at 37° C. The next day these cultures were diluted 1:10 in LB with carbenicillin (50 μg/mL) and grown at 37° C. shaking for 1 hr. Then IPTG (Isopropyl β-D-1-thiogalactopyranoside) was added to 50 μM and the cultures shaken for 4 hr at 30° C. The OD600 (optical density) of each culture was measured, and the cultures adjusted with LB to a final OD600 of 1.0. Appropriate mixtures of these cultures were made such that the % of Cry14A JM103 was 0.1%, 0.01%, 0.001%, 0.0001%, or 0%. These were then spread (30 μl each) onto either straight NGIC plates (NGIC plates are NG plates supplemented with 50 μM IPTG and 50 μg/mL carbenicillin) or NGIC plates that also included a small amount of levamisole (0.75 μg/mL in water). These plates were then used in our standard developmental assay. The dose of levamisole used is low enough such that by itself it causes no developmental delays to wild-type *C. elegans*.

The data above shows that there are elements of hypersusceptibility and/or synergism between Cry5B, Cry14A, Cry21A, and Cry6A and the entire lev/pyr/trib class of anthelmintics. This data shows that hypersusceptibility and synergy are likely to be characteristic of all nematicidal Cry proteins, which can include but is not limited to Cry14A, Cry5B, Cry21A, Cry6A, and Cry13A, in combination with lev/pyr/trib class anthelmintics. At the very least, given that Cry14A, Cry5B, Cry21A, and Cry13A (not tested here but known to be nematicidal based on Kotze et al., 2005, *Intl J Parasitol*) are all part of the same cluster of Bt Cry proteins (Wei et al., 2003, PNAS 100: 2760-2765), it is likely that all Cry proteins related to these will show hypersusceptibility and synergy with lev/pyr/trib class anthelmintics. Cry13A has 29%, 30%, and 38% amino acid identity to Cry21A, Cry5B, and Cry14A, respectively, in the toxin domain). A summary of the % sequence identity of the toxin domains of the various crystal proteins is summarized in TABLE 6 below. In summary, it is likely that any nematicidal Bt Cry proteins and any lev/pyr/trib class nAChR anthelmintics would be a powerful combination that includes synergy and hypersusceptibility as hallmarks of their interactions.

TABLE 6

Sequence Identity (%) of Various Crystal Protein Toxin Domains

| | Cry5B | Cry13A | Cry14A | Cry21A |
|---|---|---|---|---|
| Cry5B | 100 | | | |
| Cry13A | 30 | 100 | | |
| Cry14A | 34 | 38 | 100 | |
| Cry21A | 41 | 29 | 32 | 100 |

Anthelmintic Activity of Cry21A and Cry14A Against *Heligmosomoides polygyrus*

To test the ability of Cry21A to provide anthelmintic ability in vivo, two different mice strains, Balb/c (8 week males) and Swiss Webster (20-22 g females) (2 mice each), were infected per os with 150 infectious L3 larvae of the mouse parasite *H. polygyrus*. *H. polygyrus* (also known as *Nematospiroides dubius* and as *H. polygyrus bakeri*) is one of the best known rodent parasite models of intestinal nematodes and is widely used for studies of host immunology, toxicology, and pharmacology of gastrointestinal tract parasitism (Boes and Helwigh, 2000, Parasitology 121 Suppl: S97-111; Monroy and Enriquez, 1992, Parasitol Today 8:49-54.). A significant feature of this nematode-rodent system is it is the only currently used laboratory model for a chronic nematode infection in an immuno-competent mouse. *H. polygyrus* is considered a good model for direct life-cycle nematodes infecting man and veterinary animals (Boes and Helwigh, 2000, Parasitology 121 Suppl: S97-111; Monroy and Enriquez, 1992, Parasitol Today 8:49-54). The mice were gavaged on days 15, 16, and 17 postinfection (PI) with 0.1 ml of spore crystal lysates (suspended in water) from a Bt strain (4D22) engineered to produce Cry21A protein as the sole Crystal protein, achieving a final dose of 13 mg/kg Cry21A per mouse per dose. As a control, 2 mice each of Balb/c and Swiss Webster were infected with 150 infectious *H. polygyrus* larvae in parallel and were gavaged with 0.1 mL of the parent (non-Crystal-protein producing) Bt strain 4D22 on the same dates as the Cry21A gavages. Five days after the third gavage, the mice were euthanized, their small intestines removed and dissected, and the total number of intestinal worms counted. The data are shown in TABLE 7 below demonstrated that Cry21A reduced worm burdens by 48-58% and is an effective anthelmintic (for the Swiss Webster group, the Cry21A treatment gives a statistically significant difference from the control group; P=0.02).

TABLE 7

Anthelmintic activity of Cry21A against *H. polygyrus*

| Mouse Strain | Experimental Group | Intestinal worm burdens (each of two mice) | Average |
|---|---|---|---|
| Balb/c | Control | 86, 120 | 103 |
| Balb/c | Cry21A | 75, 12 | 43.5 |
| Swiss Webster | Control | 124, 139 | 131.5 |
| Swiss Webster | Cry21A | 63, 75 | 69 |

Similar experiments were carried out with Cry14A and *H. polygyrus*-infected Swiss-Webster mice. The Cry14A strain was a native Bt strain that expressed Cry14A as well as the insecticidal Cry34A and Cry35A proteins. All animals received a pre-gavage of 0.1 mL cimetidine (0.4375 g cimetidine in 5 ml of 25% ethanol in 0.9% saline) 15-30 minutes prior to gavage of Cry14A (n=6 mice) or nothing (control animals; n=7 mice). Cry14A spore-crystal lysates were suspended in water for a final dose of 50 µg/kg Cry14A (in 0.1 mL). As a positive control, a separate group of animals received Cry5B spore-crystal lysates (from a Bt strain that produces only Cry5B as its sole Cry protein) suspended in water to a final dose of 3 mg/kg in 0.1 mL (n=4). Another group of mice received gavage of purified Cry5B (as per Cappello et al., 2006, PNAS) in pH 8 buffer at 13 mg/kg in 0.1 mL (n=4). Otherwise, the experiments were carried out as for Cry21A above. The results are summarized in TABLE 8 below. The average worm burdens for control mice (n=7), Cry14A-gavaged mice (n=6), Cry5B spore-crystal lysate-gavaged mice (n=4), and purified Cry5B-gavaged mice (n=4) were 83.6±13.3, 30.3±8.4, 48.0±24.8 and 51.5±22.1, respectively, the P values relative to control were <0.001, 0.003, and 0.007, respectively, and the percent reductions relative to control were 64%, 43%, and 38%, respectively. These data demonstrated that Cry14A is an effective anthelmintic and confirm and support our previously published data (Cappello et al., 2006, PNAS) that Cry5B is an effective anthelmintic. In this case, Cry5B has anthelmintic activity delivered either as spore-crystal lysate or as purified protein.

TABLE 8

| Experimental Group | Average Worm Burden | P values | % Reduction Relative to Control |
|---|---|---|---|
| Control (n = 7) | 83.6 ± 13.3 | | |
| Cry14A (n = 6) | 30.3 ± 8.4 | <0.001 | 64% |
| Cry5B (spore-crystal lysate) (n = 4) | 48.0 ± 24.8 | <0.003 | 43% |
| Cry5B (purified) (n = 4) | 51.5 ± 22.1 | <0.007 | 38% |

Production of Spore-Crystal Lysates for Anthlemintic Gavage Experiments.

Bt strains are grown overnight from a single colony in 10 ml cultures of LB broth (Cry14A strain and 4D22) or in LB broth plus 10 µg/ml erythromycin to select for Cry-producing plasmid (Cry5B and Cry21A strains) and grown shaking overnight at 30° C. Four aliquots (4 ml) of the overnight culture is used to inoculate 200 ml of PGSM media in a 2 liter baffled flask that also contains 1 ml salts solution and 1 ml $CaCl_2$ solution (and erythromycin for Cry5B and Cry21A strains). The cultures were shaken with good aeration at 30° C. for 3-5 days and were checked for sporulation and crystal production by microscopy. The cultures should be lysed cells, phase bright spores, and phase dark crystals (except for 4D22 strain where there will not be crystals). Each culture was harvested by centrifugation at 4000 rpm for 15 minutes at 4° C. The pellet was washed once with cold 0.1 M NaCl and recentrifuged as above. The pellet was washed once with cold sterile distilled water and recentrifuged as above. The pellet was resuspended in 15 ml of cold sterile distilled water and stored at −80° C. Prior to the gavage experiments, the spore-crystal lysates (or spore lysate for 4D22) were thawed at room temperature and concentrated to the desired concentration prior to gavage to give the doses listed above. Recipe for PGSM (1 liter): 7.5 g bacto-peptone, 1 g glucose, 3.4 g $KH_2PO_4$, 4.35 g $K_2HPO_4$, pH to 7.2 and autoclaved. Recipe for Salts solution (100 ml): 2.46 g $MgSO_4$, 0.04 g $MnSO_4$, 0.28 g $ZnSO_4$, 0.40 g $FeSO_4$ filter sterilize. Recipe for $CaCl_2$ solution (100 ml): 3.66 g $CaCl_2$, filter sterilize.

REFERENCES

Albonico et al., *Ann. Trop. Med. Parasitol.*, 96:717 (2002).
Albonico et al., *Int. J. Parasitol.*, 35:803 (2005).
Albonico et al., *Int. J. Parasitol.*, 34:1205 (2004).
Albonico, *Acta Trop.*, 86:233 (2003).
Areekul et al., *J. Med. Assoc. Thai.*, 53:190 (1970).
Atkinson et al., *Transgenic Res.*, 13:135 (2004).
Betz et al., *Regul. Toxicol. Pharmacol.*, 32:156 (2000).
Blasingame & Patel, In: Proceedings of Beltwide Cotton Conference 252-253 (National Cotton Council, Nashville, Tenn.; 2003).
Bockenhoff & Grundler, *Parasitology*, 109:249 (1994).
Boes and Helwigh, 2000, Parasitology 121 Suppl: S97-111.
Brown, L. A., Jones. A. K., Buckingham, S. D., Mee, C. J., and Sattelle, D. B. 2006. Contributions from *Caenorhabditis elegans* functional genetics to antiparasitic drug target identification and validation: Nicotinic acetylcholine receptors, a case study, Int J Parasitol 36: 617-624,
Brownbridge et al., *J. Invertebr. Pathol.*, 48:216 (1986).
Bungiro et al., *Am. J. Trop. Med. Hyg.*, 73:915 (2005).
Bungiro et al., *Infect. Immun.*, 72:2203 (2004).
Bungiro et al., *J. Infect. Dis.*, 183:1380 (2001).
Bustos et al., *Plant Cell*, 1:839 (1989).
Cai et al. *Science*, 275:832 (1997).
Callis et al., *Plant Physiol.*, 88:965 (1998).
Campbell, *J. Parasitology*, 49: 628 (1963).
Cappello et al., *J. Parasitol.*, 89:S158 (2003).
Chan, *Parasitol. Today*, 13:438 (1997).
Chandrawathani et al., *Trop. Anim. Health Prod.*, 35:17 (2003).
Chou, 2006, *Pharmacolog Reviews*, 58: 621-681.
Chou and Talalay 1984, *Adv. Enzyme Regul.* 22:27-55.
Chowdhury et al., *Am. J. Trop. Med. Hyg.*, 21:300 (1972).
Chu et al., *Infect. Immun.*, 72:2214 (2004).
Cliffe et al., *Science*, 308:1463 (2005).
Coles et al., *Vet. Parasitol.*, 129:345 (2005).
Coles, *Res. Vet. Sci.*, 78:99 (2005).
Crompton et al., *Acta Trop.*, 86:121 (2003).
De Clercq et al., *Am. J. Trop. Med. Hyg.*, 57:25 (1997).
de Maagd et al., *Trends Genet.*, 17:193 (2001).
De Rocher et al., *Plant Physiol.*, 117:1445 (1998).
de Silva et al., *Trends Parasitol.*, 19:547 (2003).
de Silva, *Acta Trop.*, 86:197 (2003).
Debro et al., *J. Bacteriol.*, 165:258 (1986).
Diehn et al., *Plant Physiol.*, 117:1433 (1998).
El-Alfy & Schlenk, *Toxicological Sciences*, 68:381 (2002).
Federici, *J. Invertebr. Pathol.*, 89:30 (2005).
Ferrandiz et al., *Science*, 289:436 (2000).
Fischel et al., 2006, Preclinical Report 17: 807-813.
Gantlett et al., 2007, Antiviral Res 75:188-197.
Garside et al., *Parasitology*, 98:283 (1989).
Geary, T. G. and Thompson, D. P., 2001, *Caenorhabditis elegans*: how good a model for veterinary parasites?, Vet. Parasitol 101: 371-386.
Geerts et al., *Trop. Med. Int. Health*, 6:915 (2001).
Goverse et al. *Physiological & Molecular Plant Pathology* 52:275(1998).
Griffitts et al., *Science*, 293:860 (2001).
Griffitts et al., *Science*, 307:922 (2005).
Grover et al., *Trop. Gastroenterol.*, 22:180 (2001).
Hashmi S., Tawe, W., and Lustigman, S., 2001. *Caenorhabditis elegans* and the study of gene function in parasites, Trends in Parasitol 17: 387-393.
Held et al., *Infect. Immun.*, 74:289 (2006).
Holden-Dye, L. and Walker, R. J. Anthelmintic drugs (Nov. 2, 2007), *WormBook*, ed. The *C. elegans* Research Community, WormBook, doi/10.1895/wormbook.1.143.1, http://www.wormbook.org.
Hong et al., *Plant Physiology*, 119:1165 (1999).
Horton, *Trends Parasitol.*, 19:527 (2003).

Hwang et al., *Plant Cell*, 12:1319 (2000).
Jame, C. in ISAAA Briefs No. 32 Ithaca, N.Y.; 2004.
Jung & Wyss, *Applied Microbiology & Biotechnology* 51:439 (1999).
Kaminsky, R., Ducray, P., Jung, M., Clover, R., Rufener, L., et al., 2008, A new class of anthelmintics effective against drug-resistant nematodes, Nature 452: 176-180.
Kotze et al., *Int. J. Parasitol.*, 35:1013 (2005).
Kuhlemeier et al., *Plant Cell*, 1:471 (1989).
Lifshitz & Gavrilov, *J. Toxic.—Clin. Toxicol.*, 38:799 (2000).
Lin et al., 2007, *Carcinogenesis* 28: 2521-2529.
Lochnit et al., *Biol. Chem.*, 381:839 (2000).
Marcotte et al., *Plant Cell*, 1:969, 1989).
Marroquin et al., *Genetics*, 155:1693 (2000).
McKellar et al., *Trends Parasitol.*, 20:456 (2004).
Med Lett Drugs Ther., 1189:1 (2004).
Mertz et al., *J. Am. Vet. Med. Assoc.*, 226:779 (2005).
Molyneux et al., *PLoS Med.*, 2:e336 (2005).
Monroy and Enriquez, 1992, Parasitol Today 8:49-54.
Naimov et al., *Appl. Environ. Microbiol.*, 67:5328 (2001).
Panesar & Croll, *Int'l J. Parasitology*, 10:261 (1980).
Plovie et al. *Nematology*, 5:831 (2003).
Qaim & Zilberman, *Science*, 299:900 (2003).
Reynoldson et al., *Acta Trop.*, 68:301 (1997).
Ristaino & Thomas, *Plant Disease*, 81:965 (1997).
Roshal et al., *EMBO J.*, 6: 1155 (1987).
Saathoff et al., *BMC Infect. Dis.*, 4:27 (2004).
Sambrook et al., in, Vol. 2 9.31-39.57 (Cold Spring Harbor Laboratory Press, NY; 1989).
Sasser & Freckman, Edn. Veech, J. A. Dickerson, D. W. 7-14 (Society of Nematologists, Hyattsville, Md., USA; 1987).
Savioli et al., *Lancet*, 365:1520 (2005).
Savioli et al., *Nat. Rev. Microbiol.*, 2:618 (2004).
Savioli et al., *Parasitol. Int.*, 53:103 (2004).
Schernthaner et al., *EMBO J.*, 7:1249 (1988).
Speijer & De Waele, Vol. 1997, Edn. http://www.inibap.org/publications/technicalguidelines/guideline_eng.htm (International Network for the Improvement of Banana and Plantain, 1997).
Urbani et al., *Acta Trop.*, 86:215 (2003).
Urwin et al., *Molecular Breeding*, 6:257 (2000).
Urwin et al., *Molecular Plant-Microbe Interactions*, 15:747 (2002).
Urwin et al., *Plant Journal*, 12:455 (1997).
Urwin et al., *Plant Journal*, 8:121 (1995).
Urwin et al., *Planta*, 204:472 (1998).
Utzinger et al., *Expert Opin. Pharmacother.*, 5:263 (2004).
von Samson-Himmelstjerna et al., *Vet. Parasitol.*, 132:223 (2005).
Wakelin, *Parasitology*, 57:515 (1967)
Wei et al., *Proc. Natl. Acad. Sci. USA*, 100:2760 (2003).
Whalon et al., *Arch. Insect. Biochem. Physiol.*, 54:200 (2003).
WHO (2000) Report by secretariat. 27 Oct. 2000. Division of Communicable Diseases, EB 107/31.
Williamson & Hussey, *Plant Cell*, 8:1735 (1996).
Wolstenholme et al., *Trends Parasitol.*, 20:469 (2004).
Wu et al., *FEBS Letters*, 473:227 (2000).
Wyles et al., 2008, Antimicrob Agents Chemotherapy 52: 1862-1864.
Yoshida et al., *Am. J. Trop. Med. Hyg.*, 17:378 (1968).
Zhao et al., 2004, Clinical Cancer Res 10:7994-8004.

All publications, patents, and patent applications mentioned in this application are expressly incorporated herein by reference in their entirety. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A pharmaceutical composition comprising at least one crystal protein selected from the group consisting of Cry5B, Cry21A, Cry14A, Cry13A and Cry6A and a nicotinic acetylcholine L-type receptor agonist selected from the group consisting of levamisole, pyrantel and tribendimidine, in amounts that are synergistically effective to inhibit a parasitic worm or helminth infection in a mammal.

2. The pharmaceutical composition of claim 1, wherein the at least one crystal protein is isolated from *Bacillus thuringiensis*.

3. The pharmaceutical composition of claim 1, wherein the nicotinic acetylcholine receptor agonist is levamisole.

4. The pharmaceutical composition of claim 1, wherein the nicotinic acetylcholine receptor agonist is pyrantel or tribendimidine.

5. A method for treating a parasitic worm or helminth infection in a subject, comprising:
    administering to the subject synergistically effective amounts of at least one crystal protein selected from the group consisting of Cry5B, Cry21A, Cry14A, Cry13A and Cry6A and a nicotinic acetylcholine L-type receptor agonist selected from the group consisting of levamisole, pyrantel and tribendimidine.

6. The method of claim 5, wherein the at least one crystal protein is isolated from *Bacillus thuringiensis*.

7. The method of claim 5, wherein the parasitic worm or helminth infection is caused by a parasitic worm or helminth selected from the group consisting of Roundworm, Whipworm, Hookworm, *Ascaris*, Pinworm, *Strongyloides*, Schistosome, and Trematodes.

8. The method of claim 5, wherein the at least one crystal protein and the nicotinic acetylcholine receptor agonist is administered in a single formulation.

9. The method of claim 5, wherein the at least one crystal protein and the nicotinic acetylcholine receptor agonist are administered in separate formulations.

10. The method of claim 5, wherein synergistically effective amounts of Cry5B, Cry14 or Cry21A and the nicotinic acetylcholine receptor agonist selected from the group consisting of levamisole, pyrantel and tribendimidine are administered.

* * * * *

UNITED STATES PATENT AND TRADEMARK OFFICE
CERTIFICATE OF CORRECTION

PATENT NO. : 8,809,268 B2
APPLICATION NO. : 13/126709
DATED : August 19, 2014
INVENTOR(S) : Aroian et al.

Page 1 of 1

It is certified that error appears in the above-identified patent and that said Letters Patent is hereby corrected as shown below:

In the Specification

In column 1, line 51, delete "STNS" and insert --STNs--, therefor

In column 11, line 60, delete "(STNS)" and insert --(STNs)--, therefor

In column 27, line 26, delete "2%" and insert --$\geq 32\%$--, therefor

In the Claims

In column 34, line 54, in Claim 10, delete "Cry14" and insert --Cry14A--, therefor Signed and Sealed this
Twenty-fifth Day of November, 2014

Michelle K. Lee
*Deputy Director of the United States Patent and Trademark Office*